(12) United States Patent
Cady

US011583386B2

(10) Patent No.: US 11,583,386 B2
(45) Date of Patent: *Feb. 21, 2023

(54) INTRAOCULAR PSEUDOPHAKIC CONTACT LENS WITH MECHANISM FOR SECURING BY ANTERIOR LEAFLET OF CAPSULAR WALL AND RELATED SYSTEM AND METHOD

(71) Applicant: OnPoint Vision, Inc., Aliso Viejo, CA (US)

(72) Inventor: Kevin J. Cady, Laguna Hills, CA (US)

(73) Assignee: OnPoint Vision, Inc., Aliso Viejo, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/342,215

(22) Filed: Jun. 8, 2021

(65) Prior Publication Data
US 2021/0290369 A1 Sep. 23, 2021

Related U.S. Application Data

(63) Continuation of application No. 16/717,304, filed on Dec. 17, 2019, now Pat. No. 11,109,957, which is a
(Continued)

(51) Int. Cl.
*A61F 2/16* (2006.01)

(52) U.S. Cl.
CPC .......... *A61F 2/1602* (2013.01); *A61F 2/1648* (2013.01); *A61F 2/1613* (2013.01);
(Continued)

(58) Field of Classification Search
CPC ...... A61F 2/1602; A61F 2/161; A61F 2/1694; A61F 2/1613; A61F 2/1648;
(Continued)

(56) References Cited

U.S. PATENT DOCUMENTS 4,124,905 A 11/1978 Clark
5,071,432 A 12/1991 Baikoff
(Continued)

FOREIGN PATENT DOCUMENTS

AU 2014202532 A1 7/2014
BR PI1005015 A2 4/2013
(Continued)

OTHER PUBLICATIONS

Office Action dated Oct. 12, 2021 in connection with Mexican Patent Application No. MX/a/2017/003760, 7 pages.
(Continued)

*Primary Examiner* — Javier G Blanco

(57) ABSTRACT

An apparatus includes an intraocular pseudophakic contact lens having an optical lens and haptics extending radially from the optical lens and configured to be inserted under an anterior leaflet of a capsular wall in an eye in order to capture and confine the haptics under the anterior leaflet and secure the intraocular pseudophakic contact lens against an artificial intraocular lens in the eye. Anterior surfaces of the haptics are configured to contact an inner capsular wall surface at the anterior leaflet. Posterior surfaces of the haptics include ridges configured to capture at least one edge of the artificial intraocular lens in order to secure the intraocular pseudophakic contact lens to the artificial intraocular lens. Different portions of the optical lens provide different amounts of magnification such that a first portion of the optical lens provides a first amount of magnification and a second portion of the optical lens provides a second amount of magnification.

20 Claims, 16 Drawing Sheets

Related U.S. Application Data continuation-in-part of application No. 16/398,627, filed on Apr. 30, 2019, now Pat. No. 10,945,832, which is a continuation-in-part of application No. 15/646,254, filed on Jul. 11, 2017, now Pat. No. 10,299,910, which is a continuation-in-part of application No. 14/860,629, filed on Sep. 21, 2015, now Pat. No. 10,159,562.

(60) Provisional application No. 62/053,771, filed on Sep. 22, 2014.

(52) U.S. Cl.
CPC ........... *A61F 2/1618* (2013.01); *A61F 2/1694* (2013.01); *A61F 2002/16902* (2015.04); *A61F 2002/169051* (2015.04); *A61F 2220/0016* (2013.01); *A61F 2220/0025* (2013.01); *A61F 2250/0097* (2013.01)

(58) Field of Classification Search
CPC .... A61F 2002/16902; A61F 2002/1681; A61F 2002/1689; A61F 2002/169; A61F 2220/0025; A61F 2220/0016
See application file for complete search history.

(56) References Cited

U.S. PATENT DOCUMENTS

| | | |
|---|---|---|
| 5,078,742 A | 1/1992 | Dahan |
| 5,098,444 A | 3/1992 | Feaster |
| 5,133,747 A | 7/1992 | Feaster |
| 5,201,762 A | 4/1993 | Hauber |
| 5,217,491 A | 6/1993 | Vanderbilt |
| 5,266,241 A | 11/1993 | Parekh |
| 5,275,623 A | 1/1994 | Sarfarazi |
| 5,354,334 A | 10/1994 | Fedorov et al. |
| 5,358,520 A | 10/1994 | Patel |
| 5,443,506 A | 8/1995 | Garabet |
| 5,443,507 A | 8/1995 | Jacobi |
| 5,522,891 A | 6/1996 | Klaas |
| 5,539,016 A | 7/1996 | Kunzier et al. |
| 5,684,560 A | 11/1997 | Roffman et al. |
| 5,693,095 A | 12/1997 | Freeman et al. |
| 5,699,142 A | 12/1997 | Lee et al. |
| 5,728,156 A | 3/1998 | Gupta |
| 5,755,786 A | 5/1998 | Woffinden et al. |
| 5,769,890 A | 6/1998 | McDonald |
| 5,782,911 A | 7/1998 | Herrick |
| 5,814,103 A | 9/1998 | Lipshitz et al. |
| 5,824,074 A | 10/1998 | Koch |
| 6,027,531 A | 2/2000 | Tassignon |
| 6,030,416 A | 2/2000 | Huo et al. |
| 6,045,577 A | 4/2000 | Woffinden et al. |
| 6,113,633 A | 9/2000 | Portney |
| 6,142,625 A | 11/2000 | Sawano et al. |
| 6,169,127 B1 | 1/2001 | Lohmann et al. |
| 6,197,057 B1 | 3/2001 | Peyman et al. |
| 6,200,342 B1 | 3/2001 | Tassignon |
| 6,217,171 B1 | 4/2001 | Auten et al. |
| 6,217,612 B1 | 4/2001 | Woods |
| 6,197,058 B1 | 6/2001 | Portney |
| 6,277,146 B1 | 8/2001 | Peyman et al. |
| 6,419,697 B1 | 7/2002 | Kelman |
| 6,454,801 B1 | 9/2002 | Portney |
| 6,464,725 B2 | 10/2002 | Skotton |
| 6,488,708 B2 | 12/2002 | Sarfarazi |
| 6,554,859 B1 | 4/2003 | Lang et al. |
| 6,554,860 B2 | 4/2003 | Hoffmann et al. |
| 6,558,420 B2 | 5/2003 | Green |
| 6,582,076 B1 | 6/2003 | Roffman et al. |
| 6,616,691 B1 | 9/2003 | Tran |
| 6,616,692 B1 | 9/2003 | Glick et al. |
| 6,645,246 B1 | 11/2003 | Weinschenk, III et al. |
| 6,705,729 B2 | 3/2004 | Piers et al. |
| 6,749,634 B2 | 6/2004 | Hanna |
| 6,767,363 B1 | 7/2004 | Bandhauer et al. |
| 6,797,004 B1 | 9/2004 | Brady et al. |
| 6,818,017 B1 | 11/2004 | Shu |
| 6,827,738 B2 | 12/2004 | Willis et al. |
| 6,851,803 B2 | 2/2005 | Wooley et al. |
| 6,860,601 B2 | 3/2005 | Shadduck |
| 6,880,558 B2 | 4/2005 | Perez |
| 6,926,736 B2 | 8/2005 | Peng et al. |
| 6,952,313 B2 | 10/2005 | Schrader |
| 6,960,230 B2 | 11/2005 | Haefliger |
| 6,960,231 B2 | 11/2005 | Tran |
| 6,991,651 B2 | 1/2006 | Portney |
| 7,008,448 B2 | 3/2006 | Lipshitz et al. |
| 7,029,497 B2 | 4/2006 | Zhang et al. |
| 7,036,931 B2 | 5/2006 | Lindacher et al. |
| 7,081,134 B2 | 7/2006 | Cukrowski |
| 7,101,397 B2 | 9/2006 | Aharoni |
| 7,111,938 B2 | 9/2006 | Andino et al. |
| 7,118,597 B2 | 10/2006 | Miller et al. |
| 7,150,760 B2 | 12/2006 | Zhang |
| 7,186,266 B2 | 3/2007 | Peyman |
| 7,220,278 B2 | 5/2007 | Peyman |
| 7,223,288 B2 | 5/2007 | Zhang et al. |
| 7,238,201 B2 | 6/2007 | Portney et al. |
| 7,279,006 B2 | 10/2007 | Vincent |
| 7,311,194 B2 | 12/2007 | Jin et al. |
| 7,316,713 B2 | 1/2008 | Zhang |
| 7,338,161 B2 | 3/2008 | Chauveau et al. |
| 7,452,378 B2 | 11/2008 | Zadno-Azizi et al. |
| 7,453,646 B2 | 11/2008 | Lo |
| 7,462,193 B2 | 12/2008 | Nagamoto |
| 7,572,007 B2 | 8/2009 | Simpson |
| 7,591,849 B2 | 9/2009 | Richardson |
| 7,604,349 B2 | 10/2009 | Blum et al. |
| 7,744,647 B2 | 6/2010 | Barrett |
| 7,794,498 B2 | 9/2010 | Pinchuk |
| 7,806,929 B2 | 10/2010 | Brown |
| 7,842,087 B2 | 11/2010 | Ben Nun |
| 7,871,162 B2 | 1/2011 | Weeber |
| 7,871,437 B2 | 1/2011 | Hermans et al. |
| 7,875,661 B2 | 1/2011 | Salamone |
| 7,892,264 B2 | 2/2011 | Sanders et al. |
| 7,905,917 B2 | 3/2011 | Altmann |
| 7,918,886 B2 | 4/2011 | Aharoni et al. |
| 7,942,929 B2 | 5/2011 | Linhardt et al. |
| 7,955,704 B2 | 6/2011 | Lowery et al. |
| 8,012,204 B2 | 9/2011 | Weinschenk, III et al. |
| 8,034,107 B2 | 10/2011 | Stenger |
| 8,109,999 B2 | 2/2012 | Hampp |
| 8,133,274 B2 | 3/2012 | Zhou et al. |
| 8,197,541 B2 | 6/2012 | Schedler |
| 8,222,360 B2 | 7/2012 | Liao |
| 8,231,219 B2 | 7/2012 | Weeber |
| 8,273,123 B2 | 9/2012 | Ben Nun |
| 8,324,256 B2 | 12/2012 | Domschke et al. |
| 8,337,552 B2 | 12/2012 | Kobayashi et al. |
| 8,377,124 B2 | 2/2013 | Hong et al. |
| 8,419,791 B2 | 4/2013 | Toop |
| 8,430,928 B2 | 4/2013 | Liao |
| 8,491,651 B2 | 7/2013 | Tsai et al. |
| 8,523,942 B2 | 9/2013 | Cumming |
| 8,530,590 B2 | 9/2013 | Hu et al. |
| 8,579,972 B2 | 11/2013 | Rombach |
| 8,603,167 B2 | 12/2013 | Rombach |
| 8,608,799 B2 | 12/2013 | Blake |
| 8,636,358 B2 | 1/2014 | Binder |
| 8,680,172 B2 | 3/2014 | Liao |
| 8,696,746 B2 | 4/2014 | Wanders et al. |
| 8,834,566 B1 | 9/2014 | Jones |
| 8,852,274 B2 | 10/2014 | Doraiswamy et al. |
| 8,858,626 B2 | 10/2014 | Noy |
| 8,920,495 B2 | 12/2014 | Mirlay |
| 8,945,213 B2 | 2/2015 | Terwee et al. |
| 8,968,399 B2 | 3/2015 | Ghabra |
| 8,992,611 B2 | 3/2015 | Zhao |
| D729,390 S | 5/2015 | Doraiswamy et al. |
| 9,039,760 B2 | 5/2015 | Brady et al. |
| 9,072,600 B2 | 7/2015 | Tran |

(56) References Cited

U.S. PATENT DOCUMENTS

| | | |
|---|---|---|
| 9,084,674 B2 | 7/2015 | Brady et al. |
| D738,947 S | 9/2015 | Litovchenko |
| 9,237,946 B2 | 1/2016 | Pynson |
| 9,304,329 B2 | 4/2016 | Zhao |
| 9,329,410 B2 | 5/2016 | Riall et al. |
| 9,387,069 B2 | 7/2016 | Kahook et al. |
| 9,445,892 B2 | 9/2016 | Brown |
| 9,554,893 B2 | 1/2017 | Brady et al. |
| 9,675,445 B2 | 6/2017 | Moriarty |
| 9,757,228 B2 | 9/2017 | Wanders et al. |
| 9,808,339 B2 | 11/2017 | Diaz et al. |
| 9,820,849 B2 | 11/2017 | Jansen |
| 9,848,980 B2 | 12/2017 | McCafferty |
| 9,869,885 B2 | 1/2018 | De Sio et al. |
| 9,931,202 B2 | 4/2018 | Borja et al. |
| 9,937,034 B2 | 4/2018 | Wanders |
| 10,004,592 B2 | 6/2018 | Amon |
| 10,004,596 B2 | 6/2018 | Brady et al. |
| 10,028,824 B2 | 7/2018 | Kahook et al. |
| 10,299,910 B2 | 5/2019 | Cady |
| 10,842,614 B2 | 11/2020 | Cady |
| 11,083,622 B2 | 8/2021 | Cady et al. |
| 11,109,957 B2 | 9/2021 | Cady |
| 2002/0120329 A1 | 8/2002 | Lang et al. |
| 2002/0161436 A1 | 10/2002 | Portney |
| 2003/0158560 A1 | 8/2003 | Portney |
| 2003/0187504 A1 | 10/2003 | Weinschenk, III et al. |
| 2003/0220687 A1 | 11/2003 | Nordan et al. |
| 2004/0106993 A1 | 6/2004 | Portney |
| 2004/0158322 A1 | 8/2004 | Shen |
| 2004/0167621 A1 | 8/2004 | Peyman |
| 2004/0236422 A1 | 11/2004 | Zhang et al. |
| 2004/0249455 A1 | 12/2004 | Tran |
| 2005/0027354 A1 | 2/2005 | Brady et al. |
| 2005/0060032 A1 | 3/2005 | Magnante et al. |
| 2005/0113913 A1 | 5/2005 | Duvert |
| 2006/0001186 A1 | 1/2006 | Richardson et al. |
| 2006/0047339 A1 | 3/2006 | Brown |
| 2006/0058874 A1 | 3/2006 | Peli |
| 2006/0142856 A1 | 6/2006 | Willis et al. |
| 2006/0184244 A1 | 8/2006 | Nguyen et al. |
| 2006/0241752 A1 | 10/2006 | Israel |
| 2006/0253196 A1 | 11/2006 | Woods |
| 2006/0265059 A1 | 11/2006 | Sunada et al. |
| 2007/0010881 A1 | 1/2007 | Soye et al. |
| 2007/0016293 A1 | 1/2007 | Tran |
| 2007/0021832 A1 | 1/2007 | Nordan |
| 2007/0032866 A1 | 2/2007 | Portney |
| 2007/0118216 A1 | 5/2007 | Pynson |
| 2007/0260308 A1 | 11/2007 | Tran |
| 2007/0260309 A1 | 11/2007 | Richardson |
| 2007/0270947 A1 | 11/2007 | Peyman |
| 2007/0282438 A1 | 12/2007 | Hong et al. |
| 2008/0046077 A1 | 2/2008 | Cumming |
| 2008/0051886 A1 | 2/2008 | Lin |
| 2008/0086208 A1 | 4/2008 | Nordan |
| 2008/0103592 A1 | 5/2008 | Maloney |
| 2008/0147085 A1 | 6/2008 | Gardeski et al. |
| 2008/0208334 A1 | 8/2008 | Jinkerson et al. |
| 2008/0208335 A1 | 8/2008 | Blum |
| 2008/0215147 A1 | 9/2008 | Werblin |
| 2008/0281414 A1 | 11/2008 | Akahoshi |
| 2008/0288066 A1 | 11/2008 | Cumming |
| 2008/0312738 A1 | 12/2008 | Wanders |
| 2009/0048671 A1 | 2/2009 | Lipshitz et al. |
| 2009/0062911 A1 | 3/2009 | Bogaert |
| 2009/0130176 A1 | 5/2009 | Bossy-Nobs et al. |
| 2009/0182422 A1 | 7/2009 | Nordan et al. |
| 2009/0198326 A1 | 8/2009 | Zhou et al. |
| 2010/0004742 A1 | 1/2010 | Cumming |
| 2010/0016965 A1 | 1/2010 | Hong et al. |
| 2010/0036488 A1 | 2/2010 | de Juan, Jr. et al. |
| 2010/0094412 A1 | 4/2010 | Wensrich |
| 2010/0094413 A1 | 4/2010 | Rombach et al. |
| 2010/0131061 A1 | 5/2010 | Callahan et al. |
| 2010/0161048 A1 | 6/2010 | Schaper, Jr. |
| 2010/0161050 A1 | 6/2010 | Detmers et al. |
| 2010/0211171 A1 | 8/2010 | Sarfarazi |
| 2010/0280609 A1 | 11/2010 | Simonov et al. |
| 2010/0292789 A1 | 11/2010 | Willis et al. |
| 2011/0021733 A1 | 1/2011 | Wanders et al. |
| 2011/0153014 A1 | 6/2011 | Zhang et al. |
| 2011/0251686 A1 | 10/2011 | Masket |
| 2011/0313520 A1 | 12/2011 | Shoji et al. |
| 2011/0313521 A1 | 12/2011 | Angelopoulos |
| 2011/0313522 A1 | 12/2011 | Hayes |
| 2011/0313523 A1 | 12/2011 | Hayes |
| 2012/0109294 A1 | 5/2012 | Olson |
| 2012/0232649 A1 | 9/2012 | Cuevas |
| 2012/0253459 A1 | 10/2012 | Reich et al. |
| 2012/0323321 A1 | 12/2012 | Simonov et al. |
| 2013/0066422 A1 | 3/2013 | Dworschak et al. |
| 2013/0110234 A1 | 5/2013 | DeVita et al. |
| 2013/0110235 A1 | 5/2013 | Schwiegerling |
| 2013/0131796 A1 | 5/2013 | Mirlay |
| 2013/0190868 A1 | 7/2013 | Kahook et al. |
| 2013/0197636 A1 | 8/2013 | Haefliger |
| 2013/0204364 A1 | 8/2013 | Olson |
| 2013/0238091 A1 | 9/2013 | Danta et al. |
| 2013/0253159 A1 | 9/2013 | Benz et al. |
| 2013/0304206 A1 | 11/2013 | Pallikaris et al. |
| 2013/0317607 A1 | 11/2013 | Deboer et al. |
| 2013/0338767 A1 | 12/2013 | Mazzocchi et al. |
| 2014/0052246 A1 | 2/2014 | Kahook et al. |
| 2014/0121768 A1 | 5/2014 | Simpson |
| 2014/0180404 A1 | 6/2014 | Tran |
| 2014/0180406 A1 | 6/2014 | Simpson |
| 2014/0228949 A1 | 8/2014 | Argento et al. |
| 2014/0240657 A1 | 8/2014 | Pugh et al. |
| 2014/0243972 A1 | 8/2014 | Wanders |
| 2014/0253877 A1 | 9/2014 | Li et al. |
| 2014/0277434 A1 | 9/2014 | Weeber et al. |
| 2014/0330375 A1 | 11/2014 | McCafferty |
| 2014/0330376 A1 | 11/2014 | Kleinman |
| 2014/0347624 A1 | 11/2014 | Ando et al. |
| 2014/0368789 A1 | 12/2014 | Webb |
| 2015/0230981 A1 | 8/2015 | Kahook et al. |
| 2015/0297342 A1 | 10/2015 | Rosen et al. |
| 2016/0000558 A1 | 1/2016 | Honigsbaum |
| 2016/0008126 A1 | 1/2016 | Salahieh et al. |
| 2016/0081791 A1 | 3/2016 | Cady |
| 2016/0256265 A1 | 9/2016 | Borja et al. |
| 2016/0317286 A1 | 11/2016 | Brady et al. |
| 2016/0334643 A1 | 11/2016 | Hyde et al. |
| 2017/0172733 A1 | 6/2017 | Scharioth et al. |
| 2017/0296331 A1 | 10/2017 | Werblin et al. |
| 2017/0304045 A1 | 10/2017 | Cady |
| 2019/0254808 A1 | 8/2019 | Cady |
| 2020/0397562 A1 | 12/2020 | Cady |
| 2021/0186681 A1 | 6/2021 | Qureshi et al. |
| 2021/0282920 A1 | 9/2021 | Cady |
| 2021/0290370 A1 | 9/2021 | Cady |

FOREIGN PATENT DOCUMENTS

| | | |
|---|---|---|
| BR | 102012000755 A2 | 10/2013 |
| CN | 2717403 Y | 8/2005 |
| CN | 201015617 Y | 2/2008 |
| CN | 203425064 U | 2/2014 |
| DE | 19501444 A1 | 7/1996 |
| DE | 20109306 U1 | 8/2001 |
| DE | 10025320 A1 | 11/2001 |
| DE | 102007002885 A1 | 7/2008 |
| DE | 202010002895 U1 | 5/2010 |
| DE | 202013009162 U1 | 11/2013 |
| EP | 0760232 A1 | 3/1997 |
| EP | 1369710 A2 | 12/2003 |
| EP | 1449498 A2 | 8/2004 |
| EP | 1493405 A1 | 1/2005 |
| EP | 1504730 A1 | 2/2005 |
| EP | 1658828 A1 | 5/2006 |
| FR | 2666735 A1 | 3/1992 |
| FR | 2869793 A1 | 11/2005 |
| FR | 2966340 A1 | 4/2012 |

(56) References Cited

FOREIGN PATENT DOCUMENTS

| | | |
|---|---|---|
| FR | 2998474 A1 | 5/2014 |
| GB | 2464505 A | 4/2010 |
| GB | 2517531 A | 2/2015 |
| JP | H07255757 A | 10/1995 |
| JP | 2002360616 A | 12/2002 |
| JP | 4199573 B2 | 10/2004 |
| JP | 2006511242 A | 4/2006 |
| JP | 4363573 B2 | 11/2009 |
| JP | 4431372 B2 | 3/2010 |
| JP | 5398089 B2 | 6/2013 |
| JP | 5383782 B2 | 1/2014 |
| KR | 101555298 B1 | 9/2015 |
| RU | 2045246 C1 | 10/1995 |
| RU | 2080100 C1 | 8/1996 |
| RU | 2070004 C1 | 12/1996 |
| RU | 2129880 C1 | 5/1999 |
| RU | 2134086 C1 | 8/1999 |
| RU | 31954 U1 | 9/2003 |
| RU | 2234417 C2 | 8/2004 |
| RU | 47696 U1 | 9/2005 |
| RU | 2281063 C1 | 8/2006 |
| RU | 2281067 C1 | 8/2006 |
| RU | 2281726 C1 | 8/2006 |
| RU | 2283067 C1 | 9/2006 |
| RU | 2288494 C2 | 11/2006 |
| RU | 2377964 C2 | 1/2010 |
| RU | 2457811 C1 | 8/2012 |
| RU | 2479286 C1 | 4/2013 |
| RU | 2531472 C1 | 10/2014 |
| TW | M329428 U | 4/2008 |
| TW | 201103517 A | 2/2011 |
| WO | 91/13597 A1 | 9/1991 |
| WO | 92/15260 A1 | 9/1992 |
| WO | 94/07435 A1 | 4/1994 |
| WO | 94/13225 A1 | 6/1994 |
| WO | 96/05047 A1 | 2/1996 |
| WO | 97/12564 A1 | 4/1997 |
| WO | 99/18457 A2 | 4/1999 |
| WO | 99/35520 A1 | 7/1999 |
| WO | 99/56671 A1 | 11/1999 |
| WO | 99/62434 A1 | 12/1999 |
| WO | 00/48491 A1 | 8/2000 |
| WO | 01/08605 A1 | 2/2001 |
| WO | 01/15635 A1 | 3/2001 |
| WO | 01/87182 A2 | 11/2001 |
| WO | 2005/104994 A2 | 11/2005 |
| WO | 2006/025726 A1 | 3/2006 |
| WO | 2006/119016 A2 | 11/2006 |
| WO | 2007/138564 A1 | 12/2007 |
| WO | 2008/094518 A1 | 8/2008 |
| WO | 2010/131955 A1 | 11/2010 |
| WO | 2011/115860 A2 | 9/2011 |
| WO | 2013/055212 A1 | 4/2013 |
| WO | 2013/169652 A2 | 11/2013 |
| WO | 2014/058315 A1 | 4/2014 |
| WO | 2014/058316 A1 | 4/2014 |
| WO | 2014/071532 A1 | 5/2014 |
| WO | 2014/099338 A1 | 6/2014 |
| WO | 2014/108100 A1 | 7/2014 |
| WO | 2015/006839 A1 | 1/2015 |
| WO | 2015/022514 A1 | 2/2015 |
| WO | 2015/026226 A1 | 2/2015 |
| WO | 2015/037994 A1 | 3/2015 |
| WO | 2015/044235 A1 | 4/2015 |
| WO | 2015/066502 A1 | 5/2015 |

OTHER PUBLICATIONS

Office Action dated Jan. 3, 2022 in connection with U.S. Appl. No. 17/011,975, 20 pages.
Grant of Patent dated Jan. 17, 2022 in connection with Korean Patent Application No. 10-2021-7018671, 7 pages.
International Search Report dated Feb. 17, 2021 in connection with International Patent Application No. PCT/US2020/61099, 3 pages.
Written Opinion of the International Searching Authority dated Feb. 17, 2021 in connection with International Patent Application No. PCT/US2020/61099, 6 pages.
"1/1-DESIGNS-Questel", May 2018, 3 pages.
"1/1-DESIGNS-Questel", May 2018, 4 pages.
Extended European Search Report and Written Opinion for European Patent Application No. 15845158 dated Mar. 6, 2018, 9 pages.
International Search Report and Written Opinion of the International Searching Authority dated Aug. 30, 2018 in connection with International Patent Application No. PCT/US2018/36519, 13 pages.
International Search Report and Written Opinion of the International Searching Authority dated Dec. 21, 2015 in connection with International Patent Application No. PCT/US2015/051415, 9 pages.
Office Action dated Jun. 24, 2019 in connection with New Zealand Patent Application No. 729994, 3 pages.
Office Action dated Aug. 1, 2019 in connection with Japanese Patent Application No. 2017-535622, 11 pages.
Office Action in connection with Australian Patent Application No. 2019204613 dated Nov. 22, 2019, 3 pages.
Office Action dated Jul. 29, 2020 in connection with Australian Patent Application No. 2019204613, 3 pages.
Office Action dated May 20, 2020 in connection with Australian Patent Application No. 2018301248, 3 pages.
Communication pursuant to Article 94(3) EPC dated Jul. 15, 2020 in connection with European Patent Application No. 15845158.3, 6 pages.
Office Action dated Aug. 3, 2020 in connection with U.S. Appl. No. 16/398,627, 78 pages.
Supplementary European Search Report dated Oct. 28, 2020 in connection with European Patent Application No. 18831320, 7 pages.
Communication pursuant to Rules 70(2) and 70a(2) EPC dated Nov. 17, 2020 in connection with European Patent Application No. 18831320, 1 page.
Office Action dated Jan. 5, 2021 in connection with Japanese Patent Application No. 2020-066515, 4 pages.
Office Action dated Mar. 19, 2020 in connection with U.S. Appl. No. 16/190,959, 81 pages.
Cady et al., "Intraocular Pseudophakic Contact Lens (IOPCL)-Based Telescopic Approach for Treating Age-Related Macular Degeneration (AMD) or Other Eye Disorders", U.S. Appl. No. 17/332,533, filed May 27, 2021, 35 pages.
Examination Report dated Mar. 31, 2021 in connection with New Zealand Patent Application No. 755995, 3 pages.
Office Action dated Apr. 2, 2021 in connection with Chinese Patent Application No. 201880046413.X, 9 pages.
Notice of acceptance for patent application dated May 7, 2021 in connection with Australian Patent Application No. 2018301248, 31 pages.
Office Action dated Jul. 12, 2021 in connection with Australian Patent Application No. 2020239672, 4 pages.
European Search Report dated Jul. 16, 2021 in connection with European Patent Application No. 21161655.2, 5 pages.
Office Action dated Aug. 11, 2021 in connection with Australian Patent Application No. 2021200835, 2 pages.
Office Action dated Oct. 22, 2021 in connection with Canadian Patent Application No. 2,961,543, 5 pages.
Notice of Request for Submission of Argument dated Aug. 24, 2021 in connection with Korean Patent Application No. 10-2021-7018671, 12 pages.
European Search Report dated Sep. 2, 2021 in connection with European Patent Application No. 21168724, 7 pages.
International Search Report and Written Opinion of the International Searching Authority dated Oct. 7, 2021 in connection with International Patent Application No. PCT/US2021/037911, 9 pages.
Japanese Patent Office, Office Action dated May 25, 2022 in connection with Japanese Patent Application No. 2021-085035, 4 pages.
Japanese Patent Office, Office Action dated Jul. 20, 2022 in connection with Japanese Patent Application No. 2020-501359, 4 pages.
Examination Report No. 1 for Australian Patent Application No. AU2021245264 dated Sep. 20, 2022, 4 pages.

(56) References Cited

OTHER PUBLICATIONS

Examination Report No. 2 for Australian Patent Application No. AU2021245264 dated Nov. 23, 2022, 3 pages.

INTRAOCULAR PSEUDOPHAKIC CONTACT LENS WITH MECHANISM FOR SECURING BY ANTERIOR LEAFLET OF CAPSULAR WALL AND RELATED SYSTEM AND METHOD

CROSS-REFERENCE TO RELATED APPLICATIONS AND PRIORITY CLAIM

This application is a continuation of U.S. patent application Ser. No. 16/717,304 filed on Dec. 17, 2019, which is a continuation-in-part of U.S. patent application Ser. No. 16/398,627 filed on Apr. 30, 2019 (now U.S. Pat. No. 10,945,832), which is a continuation-in-part of U.S. patent application Ser. No. 15/646,254 filed on Jul. 11, 2017 (now U.S. Pat. No. 10,299,910), which is a continuation-in-part of U.S. patent application Ser. No. 14/860,629 filed on Sep. 21, 2015 (now U.S. Pat. No. 10,159,562), which claims priority under 35 U.S.C. § 119(e) to U.S. Provisional Patent Application No. 62/053,771 filed on Sep. 22, 2014. All of these applications are hereby incorporated by reference in their entirety.

TECHNICAL FIELD

This disclosure relates generally to implantable optical devices. More specifically, this disclosure relates to an intraocular pseudophakic contact lens with a mechanism for securing by an anterior leaflet of a capsular wall and a related system and method.

BACKGROUND

In a normal human eye, light enters through the cornea and passes through the pupil, and the natural crystalline lens focuses the light onto the retina of the eye. However, due to cataracts or other problems, the natural crystalline lens of an eye may need to be replaced with an artificial intraocular lens (IOL). The term "pseudophakia" is used to describe an eye in which the natural crystalline lens has been replaced with an intraocular lens.

Before an intraocular lens is placed into a patient's eye, a doctor or other personnel typically selects an intraocular lens that is designed to provide desired refractive correction for the patient's eye. For example, an intraocular lens could have an optical lens designed to correct myopia (near-sightedness), hyperopia (far-sightedness), astigmatism, or other refractive errors that occur naturally in the patient's eye. However, it is often the case that the intraocular lens selected for a patient's eye does not fully correct (and may even cause) some form of refractive error in the patient's eye. This refractive error is referred to as "residual" refractive error.

There are various conventional options for correcting residual refractive error, all of which have their disadvantages. For example, one intraocular lens in a patient's eye could be replaced with a different intraocular lens, but this typically has a high risk of surgical complications. Ablation surgery (such as LASIK) on the cornea of a patient's eye could be done to correct residual refractive error, but this can have a high level of unwanted side effects, particularly for older patients. An additional intraocular lens (often referred to as a "piggyback" IOL) could be inserted in front of an existing intraocular lens, but this is typically an invasive procedure with less predictability associated with the final refractive outcome. In addition, intracorneal lenses (ICLs) can be inserted into the cornea of a patient's eye, but this is often more invasive and has a high degree of rejection. In general, the above procedures are typically not predictable and have a higher degree of surgical risk. Also, the devices used in the above procedures are difficult to remove and "reverse" any residual refractive error, resulting in a higher risk of leaving the patient with induced visual aberration.

SUMMARY

This disclosure provides an intraocular pseudophakic contact lens with a mechanism for securing by an anterior leaflet of a capsular wall and a related system and method.

In a first embodiment, an apparatus includes an intraocular pseudophakic contact lens having an optical lens and haptics extending radially from the optical lens and configured to be inserted under an anterior leaflet of a capsular wall in an eye in order to capture and confine the haptics under the anterior leaflet and secure the intraocular pseudophakic contact lens against an artificial intraocular lens in the eye. Anterior surfaces of the haptics are configured to contact an inner capsular wall surface at the anterior leaflet. Posterior surfaces of the haptics include ridges configured to capture at least one edge of the artificial intraocular lens in order to secure the intraocular pseudophakic contact lens to the artificial intraocular lens. Different portions of the optical lens provide different amounts of magnification such that a first portion of the optical lens provides a first amount of magnification and a second portion of the optical lens provides a second amount of magnification.

In a second embodiment, a system includes an artificial intraocular lens having a first optical lens and first haptics configured to be implanted within a capsular bag in an eye. The system also includes an intraocular pseudophakic contact lens having a second optical lens and second haptics extending radially from the second optical lens and configured to be inserted under an anterior leaflet of a capsular wall in the eye in order to capture and confine the second haptics under the anterior leaflet and secure the intraocular pseudophakic contact lens against the artificial intraocular lens in the eye. Anterior surfaces of the second haptics are configured to contact an inner capsular wall surface at the anterior leaflet. Posterior surfaces of the second haptics include ridges configured to capture at least one edge of the artificial intraocular lens in order to secure the intraocular pseudophakic contact lens to the artificial intraocular lens. Different portions of the second optical lens provide different amounts of magnification such that a first portion of the second optical lens provides a first amount of magnification and a second portion of the second optical lens provides a second amount of magnification.

In a third embodiment, an apparatus includes an intraocular pseudophakic contact lens having an optical lens and at least three haptics extending radially from the optical lens and configured to be inserted under an anterior leaflet of a capsular wall in an eye in order to capture and confine the haptics under the anterior leaflet and secure the intraocular pseudophakic contact lens against an artificial intraocular lens in the eye. Anterior surfaces of the haptics are configured to contact an inner capsular wall surface at the anterior leaflet. Posterior surfaces of the haptics include ridges and lips projecting inward from the ridges, where the ridges and lips are configured to capture at least one edge of the artificial intraocular lens in order to secure the intraocular pseudophakic contact lens to the artificial intraocular lens. Each of the haptics includes an inner portion and an outer portion, where the inner portion of each haptic is positioned between the optical lens and the outer portion of the haptic and the inner portion of each haptic projects outward and posteriorly from the optical lens. For each haptic, the ridge is defined where a larger thickness of the outer portion of the haptic meets a smaller thickness of the inner portion of the haptic. Different portions of the optical lens provide different amounts of magnification such that a first portion of the optical lens provides a specified amount of magnification and a second portion of the optical lens provides less or no magnification relative to the specified amount of magnification.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 38, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

This disclosure provides various intraocular pseudophakic contact lenses (IOPCLs) that can be used in conjunction with intraocular lenses (IOLs). An intraocular pseudophakic contact lens generally represents a contact lens-type device that can be implanted within a patient's eye and placed on the anterior surface of an intraocular lens in the patient's eye. In some embodiments, the intraocular pseudophakic contact lens substantially corrects residual refractive error present after implantation of the intraocular lens, such as after a lensectomy (cataract) procedure. In other embodiments, the intraocular pseudophakic contact lens provides some other form of vision correction when placed on the intraocular lens in the patient's eye. In addition, the intraocular pseudophakic contact lens includes haptics or other mechanisms allowing the intraocular pseudophakic contact lens to be confined/captured by the anterior leaflet of the capsular wall in the patient's eye. In some instances, the haptics or other mechanisms can actually attach to the anterior leaflet of the capsular wall, such as through fibrosis during the healing process, to help to secure the intraocular pseudophakic contact lens in place.

Unlike conventional approaches, an intraocular pseudophakic contact lens can be implanted with less surgical risk. Moreover, an intraocular pseudophakic contact lens allows a patient to see immediately after implantation of the intraocular pseudophakic contact lens. Further, an intraocular pseudophakic contact lens can be easily replaced if a different lens is needed, such as to correct residual refractive error or to provide some other form of vision correction, or even removed if necessary. In addition, with techniques such as intraoperative wavefront aberrometry now available, refractive outcome can be measured during the actual procedure in which an intraocular pseudophakic contact lens is being implanted, which helps to identify immediately that a desired refractive target is obtained.

Figure 1:
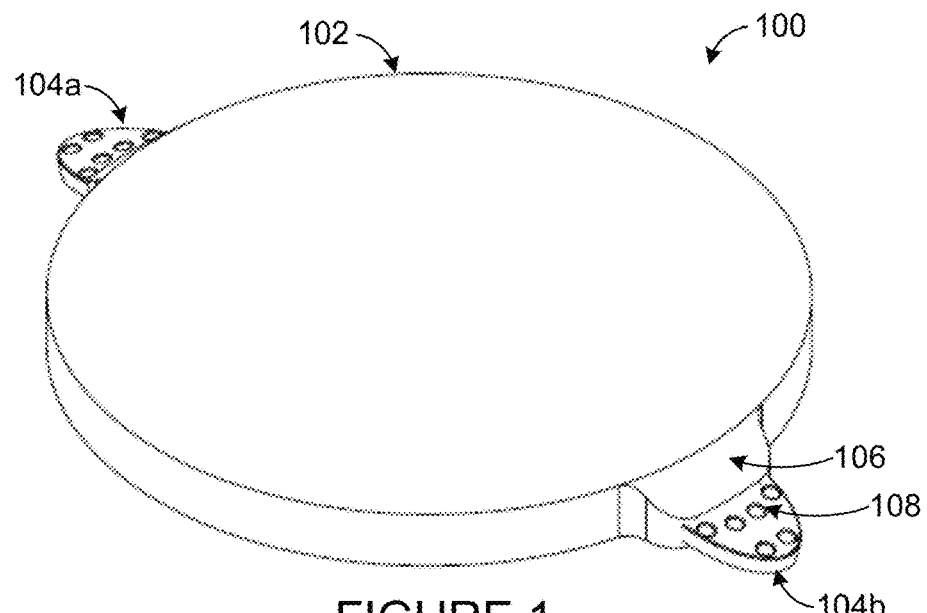
FIGS. 1 through 3 illustrate a first example intraocular pseudophakic contact lens according to this disclosure.
Figure 2:
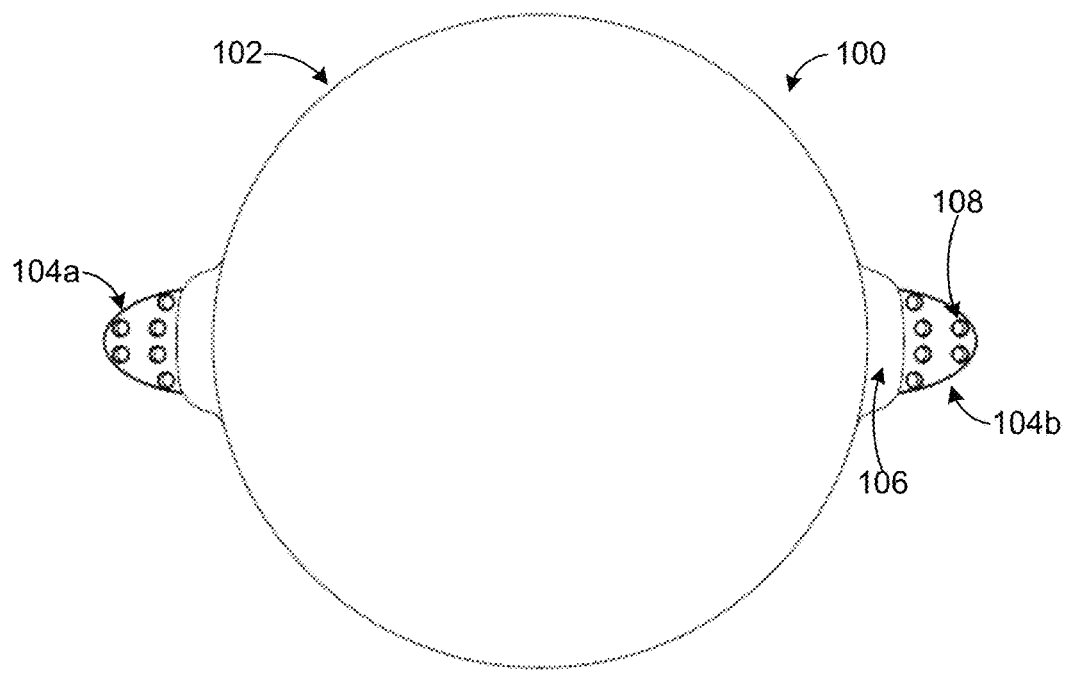
Figure 3:
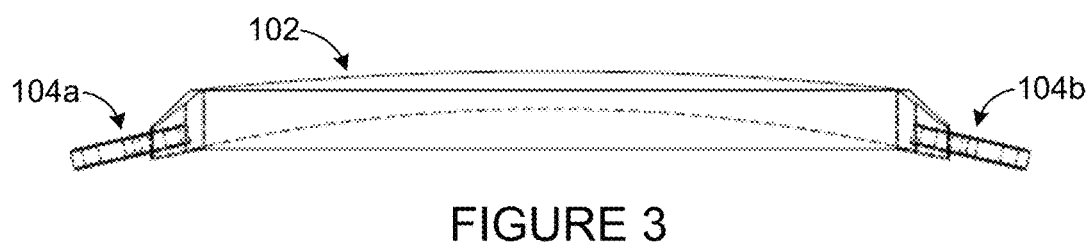

FIGS. 1 through 3 illustrate a first example intraocular pseudophakic contact lens 100 according to this disclosure. In particular, FIG. 1 illustrates an oblique view of the intraocular pseudophakic contact lens 100, FIG. 2 illustrates a top view of the intraocular pseudophakic contact lens 100, and FIG. 3 illustrates a side view of the intraocular pseudophakic contact lens 100.

As shown in FIGS. 1 through 3, the intraocular pseudophakic contact lens 100 includes an optical lens 102. The optical lens 102 denotes the portion of the intraocular pseudophakic contact lens 100 that alters light passing through the intraocular pseudophakic contact lens 100. The light that passes through the optical lens 102 then travels through an associated intraocular lens before reaching the retina of a patient's eye.

The optical lens 102 can be formed from any suitable material(s), such as silicone or acrylic. The optical lens 102 can also be formed in any suitable manner, such as by using a mold or lathe cut manufacturing process. Different lenses 102 can be designed and manufactured to provide a wide range of diopters, and each optical lens 102 can be designed to correct any suitable refractive error(s) or provide other suitable vision correction. Example types of refractive errors that can be corrected include myopia, hyperopia, and astigmatism.

The optical lens 102 in this example has a convex top surface and a concave bottom surface. However, the optical lens 102 can have any other suitable shape, which could depend (at least in part) on the type of refractive error(s) being corrected or other vision correction being made. As particular examples, the optical lens 102 could be convex, concave, spherical, aspherical, toric, mono-focal, or multi-focal. The specific lens platform used as the optical lens 102 in the intraocular pseudophakic contact lens 100 can be selected to provide the desired refractive correction or other vision correction in a patient's eye. The optical lens 102 could also include various other features as needed or desired, such as when the optical lens 102 is weighted (like at its bottom) so that the optical lens 102 orients itself on an intraocular lens in a desired orientation (like for toric platforms) or when the optical lens 102 is tinted, is photochromic, or includes an ultraviolet (UV) absorber.

Multiple haptics 104a-104b extend from multiple sides of the optical lens 102. The haptics 104a-104b are sized and shaped so that they extend a short distance from the optical lens 102 and fit under the anterior leaflet of the capsular wall in a patient's eye after implantation. Each haptic 104a-104b could be formed from any suitable material(s) and in any suitable manner. For example, each haptic 104a-104b could be formed from the same material(s) as the optical lens 102. Note that while two haptics 104a-104b are shown here, the intraocular pseudophakic contact lens 100 could include any number of haptics, including a single haptic. Also note that while the haptics 104a-104b angle downward, the haptics 104a-104b could have any other suitable arrangement.

In this example, the haptics 104a-104b are separated from the optical lens 102 by projections or extensions 106 that project from the sides of the optical lens 102. These extensions 106 represents portions of the intraocular pseudophakic contact lens 100 in which ends of the haptics 104a-104b could be embedded. Each extension 106 could be formed from any suitable material(s) and in any suitable manner. For example, each extension 106 could represent a portion of the material(s) forming the optical lens 102 and therefore represent an extension of the optical lens 102 itself. However, this need not be the case. For instance, the optical lens 102 could be placed within a retaining ring that is integral with or attached to the extensions 106, or the extensions 106 could be secured to the optical lens 102 itself using adhesive or other suitable connecting mechanism.

Note that while two extensions 106 are shown here, the intraocular pseudophakic contact lens 100 could include any number of extensions, including a single extension. Also note that the presence of the extensions 106 is not required and that the haptics 104a-104b could be integrated directly with the optical lens 102. In those embodiments, the haptics 104a-104b could represent portions of the material(s) forming the optical lens 102, although this need not be the case. For instance, the optical lens 102 could be placed within a retaining ring that is integral with or attached to the haptics 104a-104b, or the haptics 104a-104b could be secured to the optical lens 102 itself using adhesive or other suitable connecting mechanism.

Each of the haptics 104a-104b includes a textured surface 108, which in this example is formed using various holes formed partially or completely through the haptics 104a-104b. The textured surfaces 108 allow the haptics 104a-104b to be captured and confined by the anterior leaflet of the capsular wall in a patient's pseudophakic eye. In some cases, the textured surfaces 108 allow the haptics 104a-104b to actually physically bond to the anterior leaflet of the capsular wall in the patient's eye, such as through fibrosis during the healing process. The haptics 104a-104b help to secure the intraocular pseudophakic contact lens 100 in place on an intraocular lens. Note that the numbers and sizes of the holes in the textured surfaces 108 are for illustration only and that the haptics 104a-104b could include different numbers and sizes of holes. For instance, the haptics 104a-104b could include a large number of very small holes or other structures forming a texture that promotes confinement, capture, or attachment to the anterior leaflet of the capsular wall.

The anterior leaflet of the capsular wall in a patient's eye is typically created during a capsulotomy in which the natural crystalline lens in the patient's eye is removed and replaced with an intraocular lens. The anterior leaflet represents the outer portion of the front side of the capsular bag that remains after an opening (referred to as a capsulorhexis) is formed in the capsular bag so that the natural crystalline lens can be removed. In some cases, this could occur long before the intraocular pseudophakic contact lens 100 is to be implanted. After the capsulotomy, the anterior leaflet of the capsular wall typically shrinks and undergoes fibrosis during the healing process.

When the intraocular pseudophakic contact lens 100 is inserted into the patient's eye, the intraocular pseudophakic contact lens 100 can be positioned so that the haptics 104a-104b extend under the anterior leaflet in the patient's eye. This allows the haptics 104a-104b to be captured and confined by the anterior leaflet. The haptics 104a-104b could also be physically attached to the anterior leaflet over time, such as by way of a "re-fibrosis" of the anterior leaflet. This re-fibrosis of tissue will bond to and cover part or all of the haptics 104a-104b, further securing the intraocular pseudophakic contact lens 100 in place. Note, however, that the intraocular pseudophakic contact lens 100 could also be implanted during the same procedure in which the intraocular lens is being implanted. In that case, the intraocular pseudophakic contact lens 100 could be secured by the haptics 104a-104b and possibly during fibrosis (and not re-fibrosis) within the patient's eye.

Figure 4:
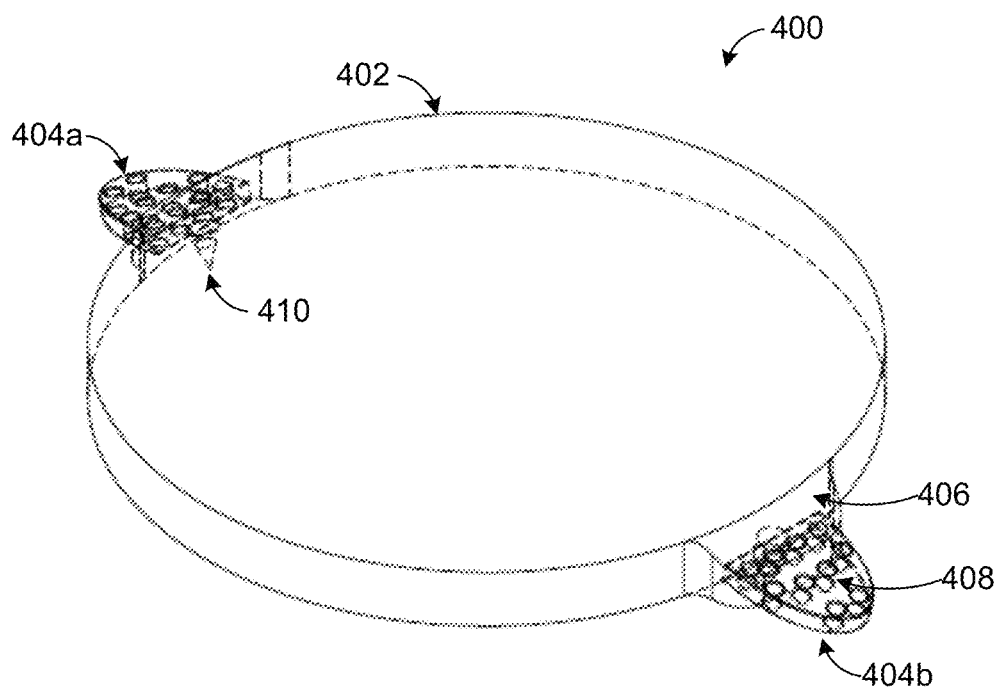
FIGS. 4 and 5 illustrate a second example intraocular pseudophakic contact lens according to this disclosure.
Figure 5:
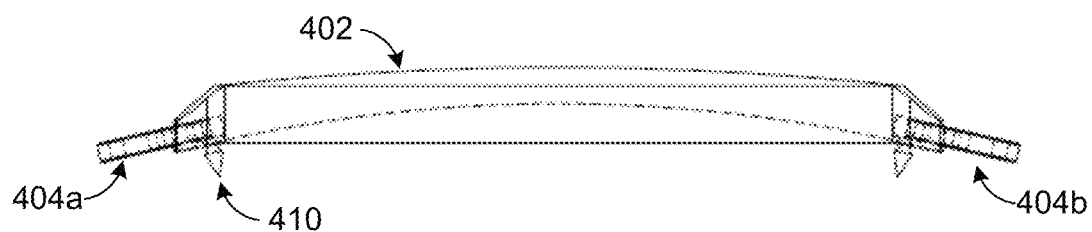

FIGS. 4 and 5 illustrate a second example intraocular pseudophakic contact lens 400 according to this disclosure. In particular, FIG. 4 illustrates an oblique view of the intraocular pseudophakic contact lens 400, and FIG. 5 illustrates a side view of the intraocular pseudophakic contact lens 400.

As shown in FIGS. 4 and 5, the intraocular pseudophakic contact lens 400 has various components that are the same as or similar to those forming the intraocular pseudophakic contact lens 100. For example, the intraocular pseudophakic contact lens 400 includes an optical lens 402, multiple haptics 404a-404b, and optionally multiple extensions 406. The haptics 404a-404b include textured surfaces 408.

The intraocular pseudophakic contact lens 400 also includes one or more pins 410. Each pin 410 projects downward from an extension 406 or from the inner end of a haptic 404a-404b. The pin(s) 410 can be used to pierce the anterior surface of an intraocular lens or to rest on the anterior surface of the intraocular lens. In addition to the capture/confinement of the haptics 404a-404b by the anterior leaflet, the pins 410 can help to further hold the intraocular pseudophakic contact lens 400 in place and resist slipping of the intraocular pseudophakic contact lens 400. In some cases, the pins 410 could be used to prevent movement of the intraocular pseudophakic contact lens 400 during the period immediately after implantation and before the haptics 404a-404b of the intraocular pseudophakic contact lens 400 have bonded to the anterior leaflet of the capsular wall in the patient's eye (such as via fibrosis).

Each pin 410 could be formed from any suitable material(s) and in any suitable manner. Note that while two pins 410 are shown here, the intraocular pseudophakic contact lens 400 could include any number of pins, including a single pin. Also note that while the pins 410 here are shown as having sharp ends, this need not be the case. For example, the pins 410 could have rounded or blunted surfaces to help the pins 410 sit on (without piercing) the anterior surface of an intraocular lens. In addition, while the pins 410 are shown here as extending through or being embedded within the extensions 406, the pins 410 could be located in any other suitable position(s). For instance, the pins 410 could be moved to the outer ends of the haptics 404a-404b, or additional pins 410 could be placed at the outer ends of the haptics 404a-404b.

As noted above, the intraocular pseudophakic contact lens 400 can be implanted during the same procedure in which an intraocular lens is being implanted or during a subsequent procedure after the intraocular lens has already been implanted in a patient's eye. The anterior leaflet of the capsular wall of the patient's eye could be used to capture and confine the haptics 404a-404b of the intraocular pseudophakic contact lens 400 under the anterior leaflet, and optionally fibrosis or re-fibrosis could occur to attach the haptics 404a-404b to the patient's eye. The pins 410 can be used to help hold the intraocular pseudophakic contact lens 400 in place.

Figure 6:
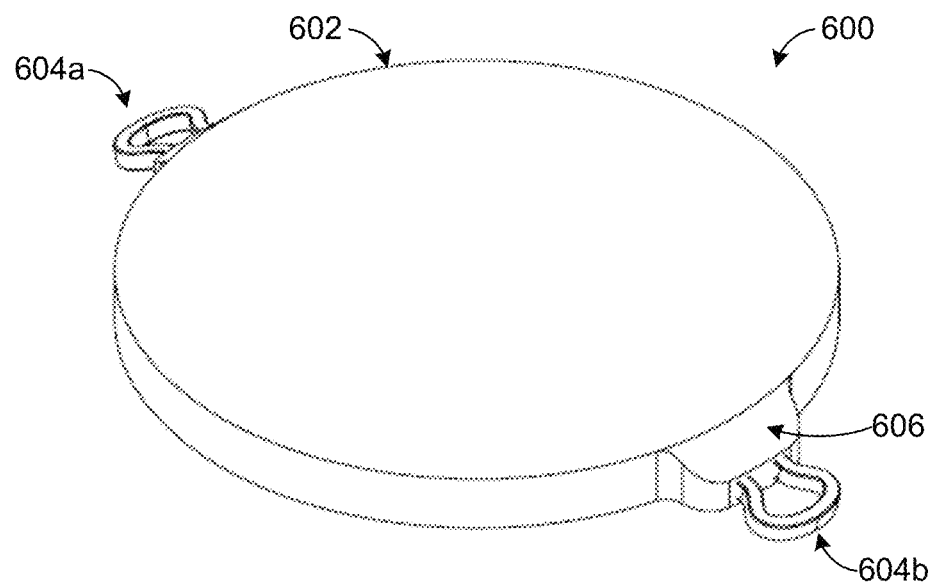
FIGS. 6 through 8 illustrate a third example intraocular pseudophakic contact lens according to this disclosure.
Figure 7:
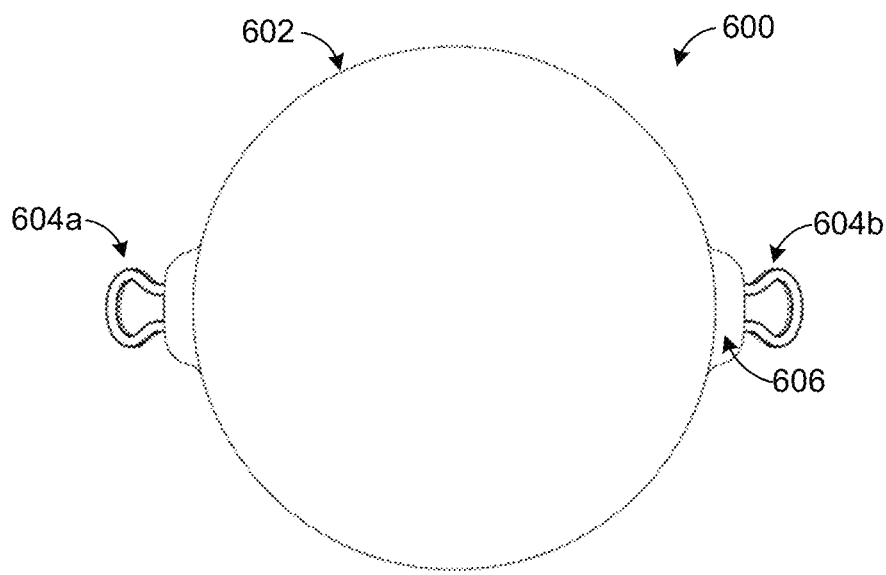
Figure 8:
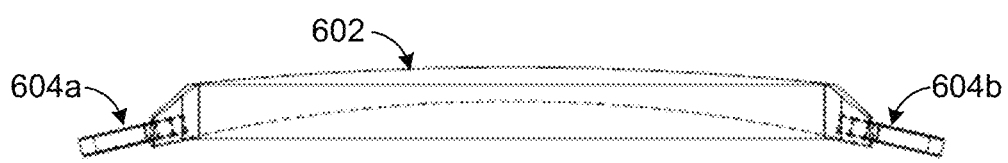

FIGS. 6 through 8 illustrate a third example intraocular pseudophakic contact lens 600 according to this disclosure. In particular, FIG. 6 illustrates an oblique view of the intraocular pseudophakic contact lens 600, FIG. 7 illustrates a top view of the intraocular pseudophakic contact lens 600, and FIG. 8 illustrates a side view of the intraocular pseudophakic contact lens 600.

As shown in FIGS. 6 through 8, the intraocular pseudophakic contact lens 600 includes an optical lens 602, which may be the same as or similar to the optical lenses 202 and 402 described above. The intraocular pseudophakic contact lens 600 also includes multiple haptics 604a-604b and optionally multiple extensions 606. The haptics 604a-604b here are formed by loops of material, such as metal or plastic. The ends of the haptics 604a-604b are embedded within the extensions 606 in this example, although the extensions 606 could be omitted and the haptics 604a-604b could be coupled to the optical lens 602 or to a retaining ring in which the optical lens 602 is placed. Note that while the haptics 604a-604b angle downward, the haptics 604a-604b could have any other suitable arrangement. Each of the haptics 604a-604b could include a textured surface that facilitates confinement, capture, or attachment to the anterior leaflet of the capsular wall.

The intraocular pseudophakic contact lens 600 can be implanted during the same procedure in which an intraocular lens is being implanted or during a subsequent procedure after the intraocular lens has already been implanted in a patient's eye. The anterior leaflet of the capsular wall of the patient's eye could be used to capture and confine the haptics 604a-604b of the intraocular pseudophakic contact lens 600 under the anterior leaflet, and optionally fibrosis or re-fibrosis could occur to attach the haptics 604a-604b to the patient's eye.

Figure 9:
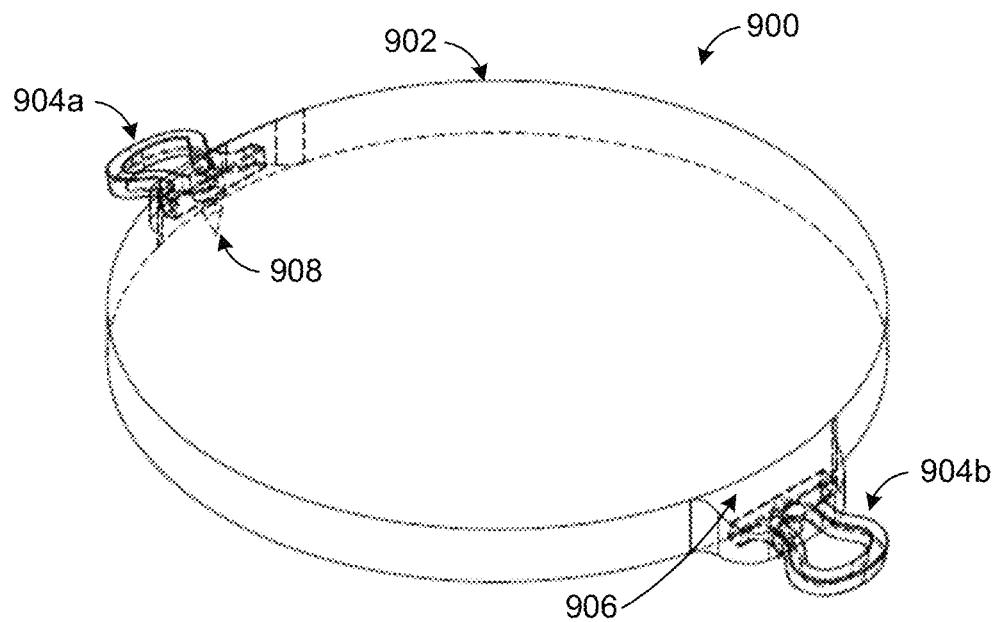
FIGS. 9 and 10 illustrate a fourth example intraocular pseudophakic contact lens according to this disclosure.
Figure 10:
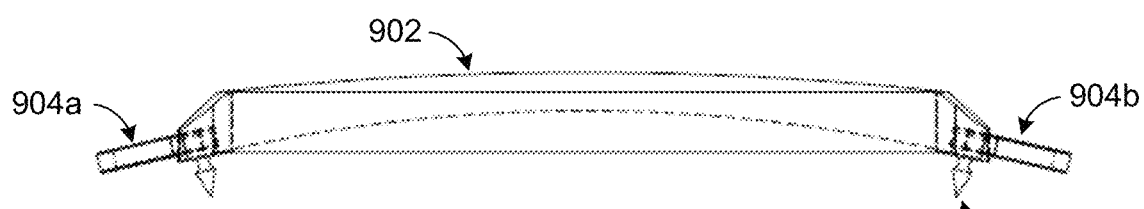

FIGS. 9 and 10 illustrate a fourth example intraocular pseudophakic contact lens 900 according to this disclosure. In particular, FIG. 9 illustrates an oblique view of the intraocular pseudophakic contact lens 900, and FIG. 10 illustrates a side view of the intraocular pseudophakic contact lens 900.

As shown in FIGS. 9 and 10, the intraocular pseudophakic contact lens 900 has various components that are the same as or similar to those forming the intraocular pseudophakic contact lens 600. For example, the intraocular pseudophakic contact lens 900 includes an optical lens 902, multiple haptics 904a-904b, and optionally multiple extensions 906. The haptics 904a-904b form small loops that are sized and shaped so that they extend a short distance from the optical lens 902 and fit under the anterior leaflet of the capsular wall in a patient's eye after implantation. Each of the haptics 904a-904b could include a textured surface that facilitates confinement, capture, or attachment to the anterior leaflet of the capsular wall.

The intraocular pseudophakic contact lens 900 also includes one or more pins 908. Each pin 908 projects downward from an extension 906 or from the inner end of a haptic 904a-904b. The pin(s) 908 can be used to pierce the anterior surface of an intraocular lens or to rest on the anterior surface of the intraocular lens. In addition to the capture/confinement of the haptics 904a-904b by the anterior leaflet, the pins 908 can help to further hold the intraocular pseudophakic contact lens 900 in place and resist slipping of the intraocular pseudophakic contact lens 900. In some cases, the pins 908 could be used to prevent movement of the intraocular pseudophakic contact lens 900 during the period immediately after implantation and before the haptics 904a-904b of the intraocular pseudophakic contact lens 900 have bonded to the anterior leaflet of the capsular wall in the patient's eye (such as via fibrosis).

Each pin 908 could be formed from any suitable material(s) and in any suitable manner. Note that while two pins 908 are shown here, the intraocular pseudophakic contact lens 900 could include any number of pins, including a single pin. Also note that while the pins 908 here are shown as having sharp ends, this need not be the case. For example, the pins 908 could have rounded or blunted surfaces to help the pins 908 sit on (without piercing) the anterior surface of an intraocular lens. In addition, while the pins 908 are shown here as extending through or being embedded within the extensions 906, the pins 908 could be located in any other suitable position(s). For instance, the pins 908 could be moved to the outer ends of the haptics 904a-904b, or additional pins 908 could be placed at the outer ends of the haptics 904a-904b.

The intraocular pseudophakic contact lens 900 can be implanted during the same procedure in which an intraocular lens is being implanted or during a subsequent procedure after the intraocular lens has already been implanted in a patient's eye. The anterior leaflet of the capsular wall of the patient's eye could be used to capture and confine the haptics 904a-904b of the intraocular pseudophakic contact lens 900 under the anterior leaflet, and optionally fibrosis or re-fibrosis could occur to attach the haptics 904a-904b to the patient's eye. The pins 908 can be used to help hold the intraocular pseudophakic contact lens 900 in place.

Figure 11:
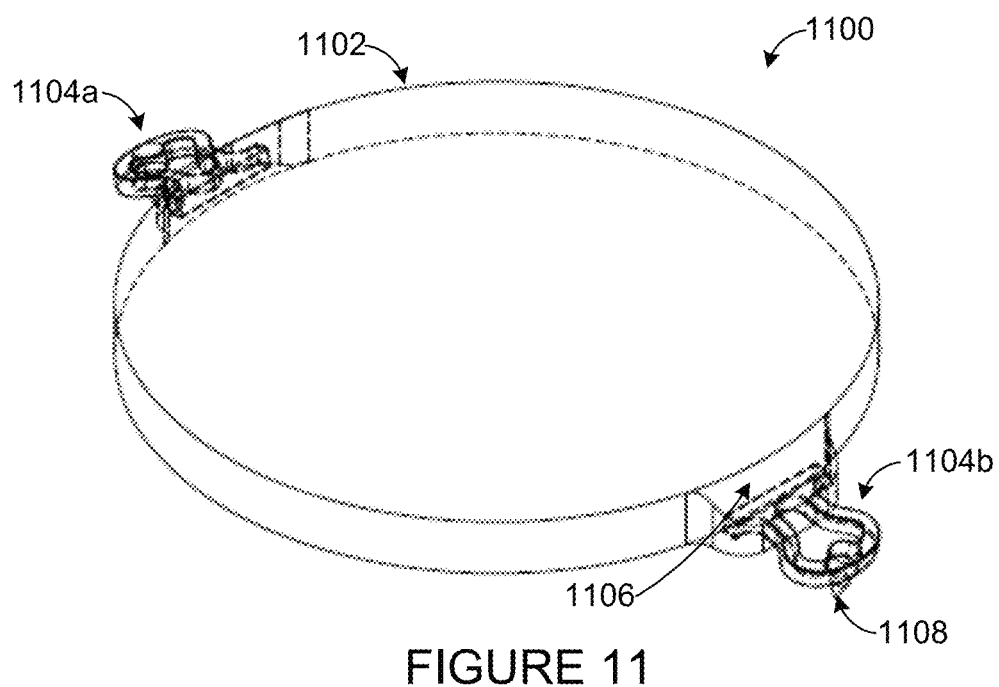
FIGS. 11 and 12 illustrate a fifth example intraocular pseudophakic contact lens according to this disclosure.
Figure 12:
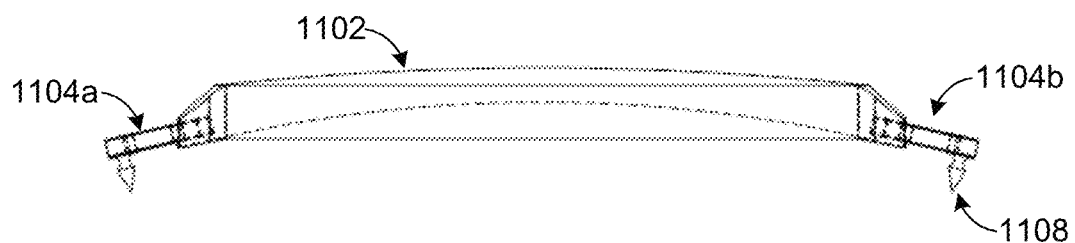

FIGS. 11 and 12 illustrate a fifth example intraocular pseudophakic contact lens 1100 according to this disclosure. In particular, FIG. 11 illustrates an oblique view of the intraocular pseudophakic contact lens 1100, and FIG. 12 illustrates a side view of the intraocular pseudophakic contact lens 1100.

As shown in FIGS. 11 and 12, the intraocular pseudophakic contact lens 1100 has various components that are the same as or similar to those forming the intraocular pseudophakic contact lens 900. For example, the intraocular pseudophakic contact lens 1100 includes an optical lens 1102, multiple haptics 1104a-1104b, and optionally multiple extensions 1106. The haptics 1104a-1104b form small loops that are sized and shaped so that they extend a short distance from the optical lens 1102 and fit under the anterior leaflet of the capsular wall in a patient's eye after implantation.

Each of the haptics 1104a-1104b could include a textured surface that facilitates confinement, capture, or attachment to the anterior leaflet of the capsular wall.

The intraocular pseudophakic contact lens 1100 also includes one or more pins 1108. Each pin 1108 projects downward from the outer end of a haptic 1104a-1104b. The pins 1108 are therefore positioned farther away from the optical lens 1102 compared to the pins 908. This may allow the intraocular pseudophakic contact lens 1100 to be used with larger intraocular lenses. This may also allow the pins 1108 to extend to or beyond the edges of an intraocular lens, which could help the intraocular pseudophakic contact lens 1100 to lock onto the anterior surface or sides of the intraocular lens or to reduce sliding of the intraocular pseudophakic contact lens 1100 on the intraocular lens.

The intraocular pseudophakic contact lens 1100 can be implanted during the same procedure in which an intraocular lens is being implanted or during a subsequent procedure after the intraocular lens has already been implanted in a patient's eye. The anterior leaflet of the capsular wall of the patient's eye could be used to capture and confine the haptics 1104a-1104b of the intraocular pseudophakic contact lens 1100 under the anterior leaflet, and optionally fibrosis or re-fibrosis could occur to attach the haptics 1104a-1104b to the patient's eye. The pins 1108 can be used to help hold the intraocular pseudophakic contact lens 1100 in place.

Figure 13:
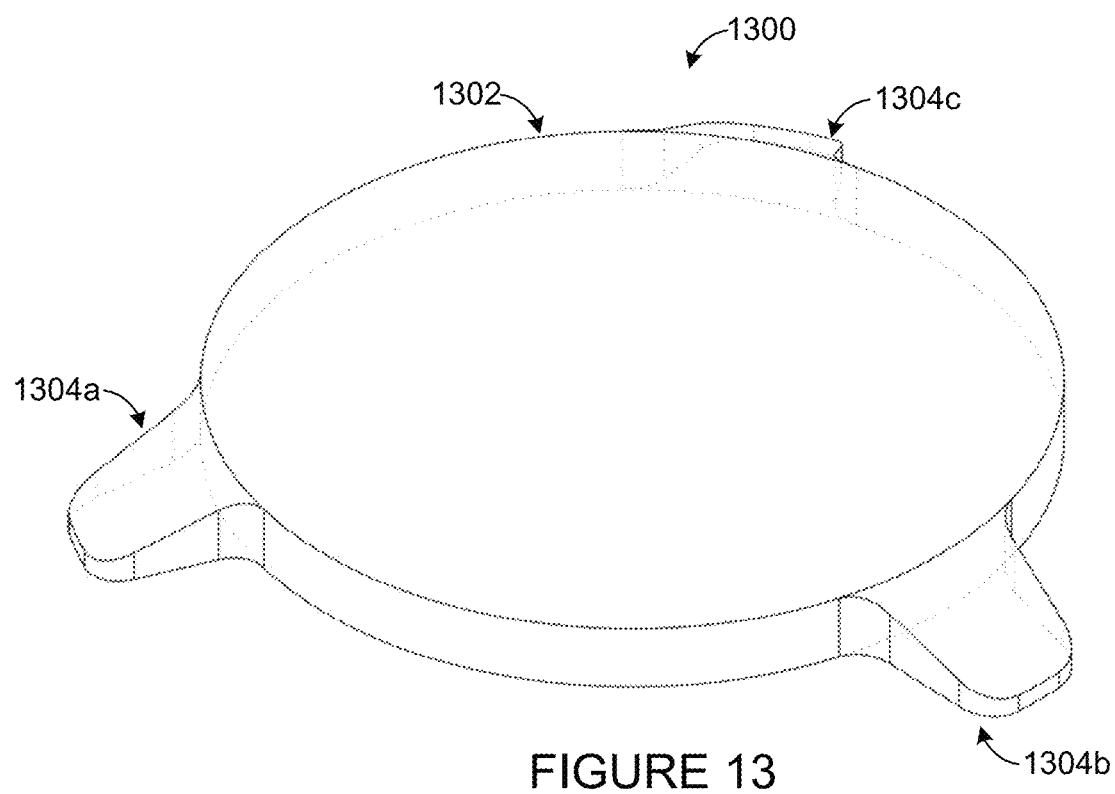
FIG. 13 illustrates a sixth example intraocular pseudophakic contact lens according to this disclosure.

FIG. 13 illustrates a sixth example intraocular pseudophakic contact lens 1300 according to this disclosure. As shown in FIG. 13, the intraocular pseudophakic contact lens 1300 includes an optical lens 1302 and multiple haptics 1304a-1304c. The optical lens 1302 could be the same as or similar to the various optical lenses described above.

In this example, the haptics 1304a-1304c are formed by large projections that extend from the sides of the optical lens 1302, where the projections have a thickness that tapers towards the outer edges of the projections. This facilitates easier insertion of the haptics 1304a-1304c under the anterior leaflet of the capsular wall in a patient's eye. Each of the haptics 1304a-1304c could include a textured surface, such as a number of holes or other structures, that promotes confinement, capture, or attachment to the anterior leaflet of the capsular wall. While three haptics 1304a-1304c are shown here, other numbers of haptics could also be used.

Figure 14:
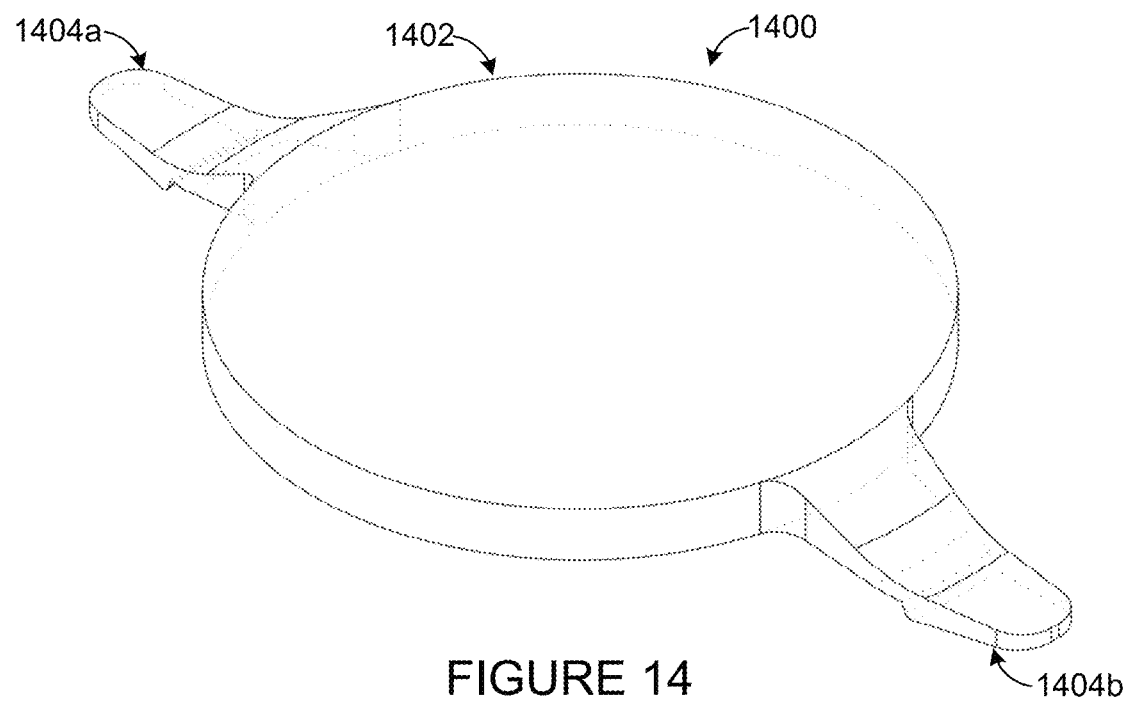
FIGS. 14 and 15 illustrate a seventh example intraocular pseudophakic contact lens according to this disclosure.
Figure 15:
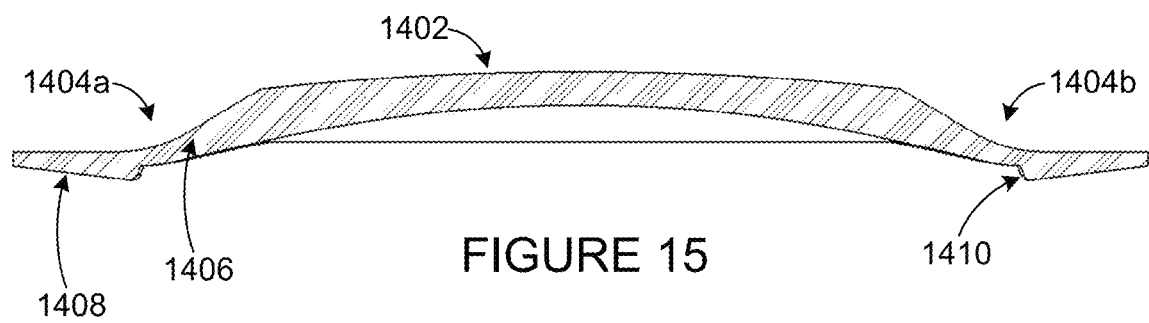

FIGS. 14 and 15 illustrate a seventh example intraocular pseudophakic contact lens 1400 according to this disclosure. In particular, FIG. 14 illustrates an oblique view of the intraocular pseudophakic contact lens 1400, and FIG. 15 illustrates a cross-sectional view through the middle of the intraocular pseudophakic contact lens 1400.

As shown in FIGS. 14 and 15, the intraocular pseudophakic contact lens 1400 includes an optical lens 1402 and multiple haptics 1404a-1404b. The optical lens 1402 could be the same as or similar to the various optical lenses described above. Each of the haptics 1404a-1404b could include a textured surface, such as a number of holes or other structures, that promotes confinement, capture, or attachment to the anterior leaflet of the capsular wall.

In this example, the haptics 1404a-1404b are formed by larger projections that extend from the sides of the optical lens 1402. Each haptic 1404a-1404b includes an inner portion 1406 that is connected to the optical lens 1402 and an outer portion 1408 that is connected to the inner portion 1406, effectively forming long "wings" extending from the optical lens 1402. The outer portions 1408 have a thickness that tapers towards the outer edges of the haptics 1404a-1404b, which facilitates easier insertion of the haptics 1404a-1404b under the anterior leaflet of the capsular wall in a patient's eye. The inner portion 1406 projects outward and downward in this example, while the outer portion 1408 projects outward and slightly upward in this example (although other forms could also be used). This shape allows the haptics 1404a-1404b to be used with larger intraocular lenses while still extending under the anterior leaflet of the capsular wall.

Each of the haptics 1404a-1404b also includes a ridge 1410, and multiple ridges 1410 of multiple haptics 1404a-1404b can be used to capture one or more edges of the underlying intraocular lens. This can help to center the intraocular pseudophakic contact lens 1400 on the intraocular lens. This can also help to retain the intraocular pseudophakic contact lens 1400 in place on the intraocular lens during the healing process.

Figure 16:
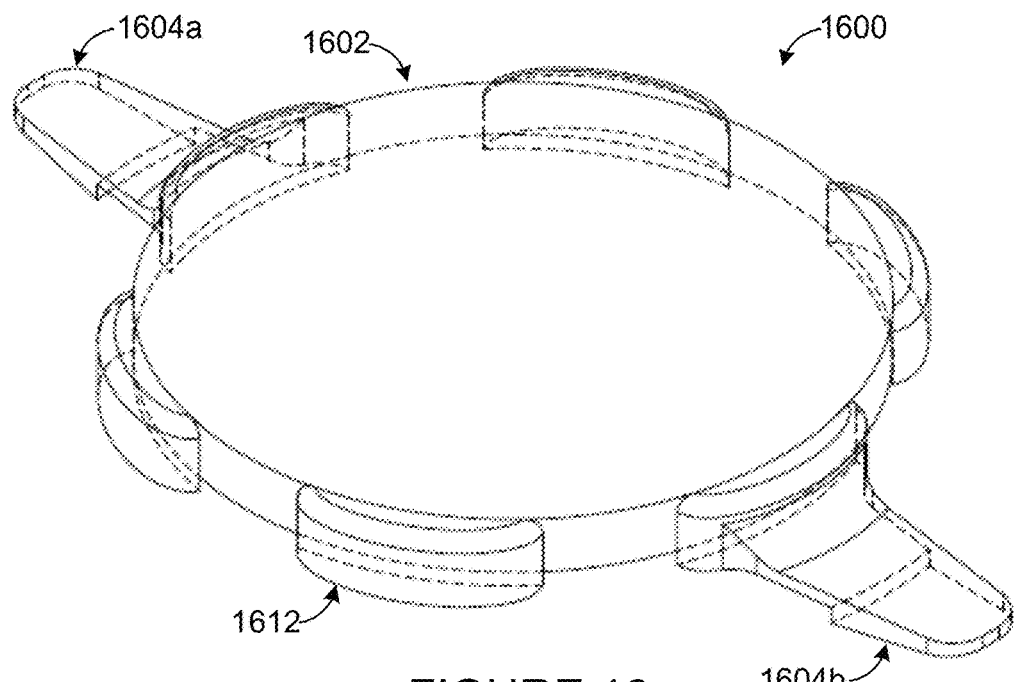
FIGS. 16 through 18 illustrate an eighth example intraocular pseudophakic contact lens according to this disclosure.
Figure 17:
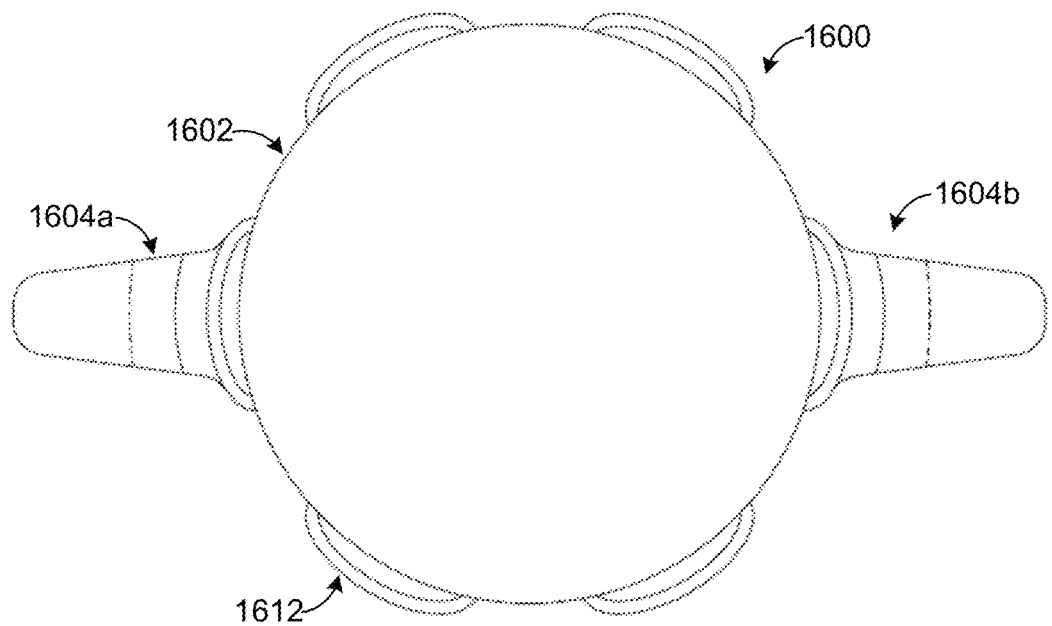
Figure 18:
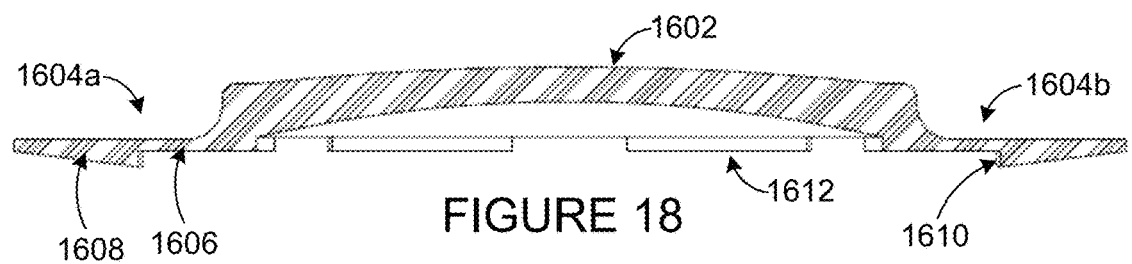

FIGS. 16 through 18 illustrate an eighth example intraocular pseudophakic contact lens 1600 according to this disclosure. In particular, FIG. 16 illustrates an oblique view of the intraocular pseudophakic contact lens 1600, FIG. 17 illustrates a top view of the intraocular pseudophakic contact lens 1600, and FIG. 18 illustrates a cross-sectional view through the middle of the intraocular pseudophakic contact lens 1600.

As shown in FIGS. 16 through 18, the intraocular pseudophakic contact lens 1600 has various components that are the same as or similar to those forming the intraocular pseudophakic contact lens 1400. For example, the intraocular pseudophakic contact lens 1600 includes an optical lens 1602 and multiple haptics 1604a-1604b. The haptics 1604a-1604b are formed by larger projections that extend from the sides of the optical lens 1602. Each haptic 1604a-1604b includes an inner portion 1606 that is connected to the optical lens 1602 (or to a retaining ring in which the optical lens 1602 is located) and an outer portion 1608 that is connected to the inner portion 1606. The outer portions 1608 have a thickness that tapers towards the outer edges of the haptics 1604a-1604b, which facilitates easier insertion of the haptics 1604a-1604b under the anterior leaflet of the capsular wall in a patient's eye. The inner portion 1606 and the outer portion 1608 both project outward and straight in this example (although other forms could also be used). This shape allows the haptics 1604a-1604b to be used with larger intraocular lenses while still extending under the anterior leaflet of the capsular wall.

Each of the haptics 1604a-1604b also includes a ridge 1610, and multiple ridges 1610 of multiple haptics 1604a-1604b can be used to capture one or more edges of the underlying intraocular lens. This can help to center the intraocular pseudophakic contact lens 1600 on the intraocular lens. This can also help to retain the intraocular pseudophakic contact lens 1600 in place on the intraocular lens during the healing process.

In addition, the intraocular pseudophakic contact lens 1600 here includes multiple segments 1612 located along the sides of the optical lens 1602. The segments 1612 denote projections from the optical lens 1602, and at least some of the segments 1612 could be coupled to the haptics 1604a-1604b (such as when ends of the haptics 1604a-1604b are embedded in the segments 1612). The segments 1612 extend downward so that the bottom surfaces of the segments 1612 are located below the optical lens 1602. As a result, when implanted into a patient's eye, the segments 1612 keep the optical lens 1602 separated from the underlying intraocular lens. Depending on the shape of the posterior surface of the optical lens 1602 and the shape of the anterior surface of the underlying intraocular lens, this could elevate the optical lens 1602 over an optical lens within the underlying intraocular lens so that the optical lenses do not contact each other.

Each of the segments 1612 could be formed from any suitable material(s) and in any suitable manner. For example, each segment 1612 could represent a portion of the material(s) forming the optical lens 1602 and therefore represent an extension of the optical lens 1602 itself. However, this need not be the case. For instance, the optical lens 1602 could be placed within a retaining ring that is integral with or attached to the segments 1612, or the segments 1612 could be secured to the optical lens 1602 itself using adhesive or other suitable connecting mechanism. Each of the segments 1612 could also have any suitable size, shape, and dimensions. For example, the segments 1612 could be smaller or larger (relative to the other structures) than what is shown in FIGS. 16 through 18. As another example, the segments 1612 could denote curved structures that leave small open areas between the segments 1612 and the optical lens 1602, or the segments 1612 could be solid structures that leave no open areas between the segments 1612 and the optical lens 1602.

The ability to space the optical lens 1602 away from the underlying intraocular lens could provide various benefits. For example, elevating the optical lens 1602 over the underlying intraocular lens may allow for an increase in aqueous flow between the anterior surface of the intraocular lens and the posterior surface of the optical lens 1602. An increased flow of aqueous between the lenses could help to reduce lens deposits on either or both of the lenses. Also, the presence of aqueous between the lenses can help to improve the optic or image quality of the combined lens system. In addition, by providing more space between the lenses, the intraocular pseudophakic contact lens 1600 could be used with a wider range of intraocular lenses that have varying anterior curvature surfaces, allowing the intraocular pseudophakic contact lens 1600 to be used with a wider range of intraocular lens models and powers.

Figure 19:
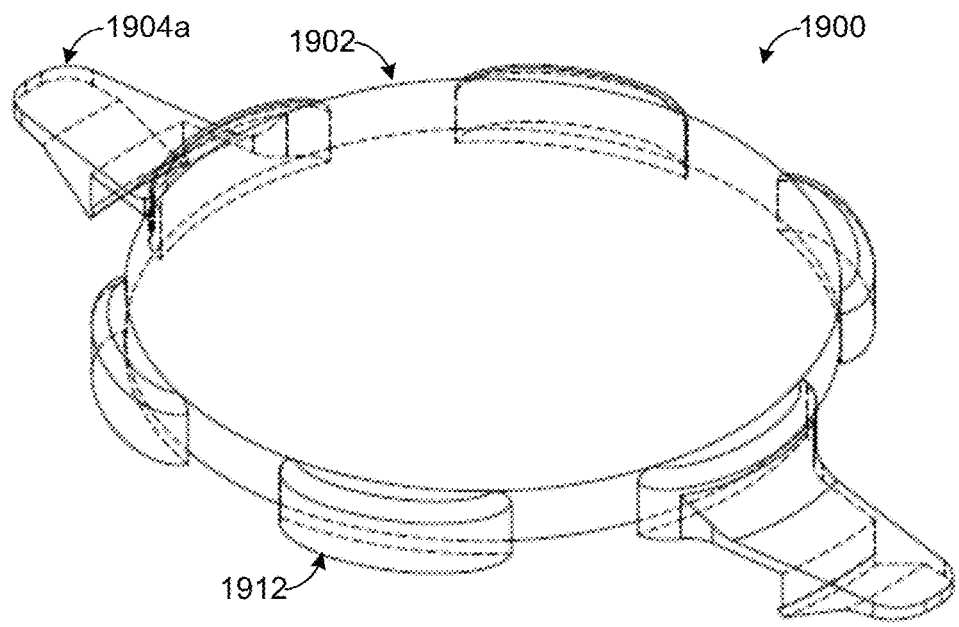
FIGS. 19 through 21 illustrate a ninth example intraocular pseudophakic contact lens according to this disclosure.
Figure 20:
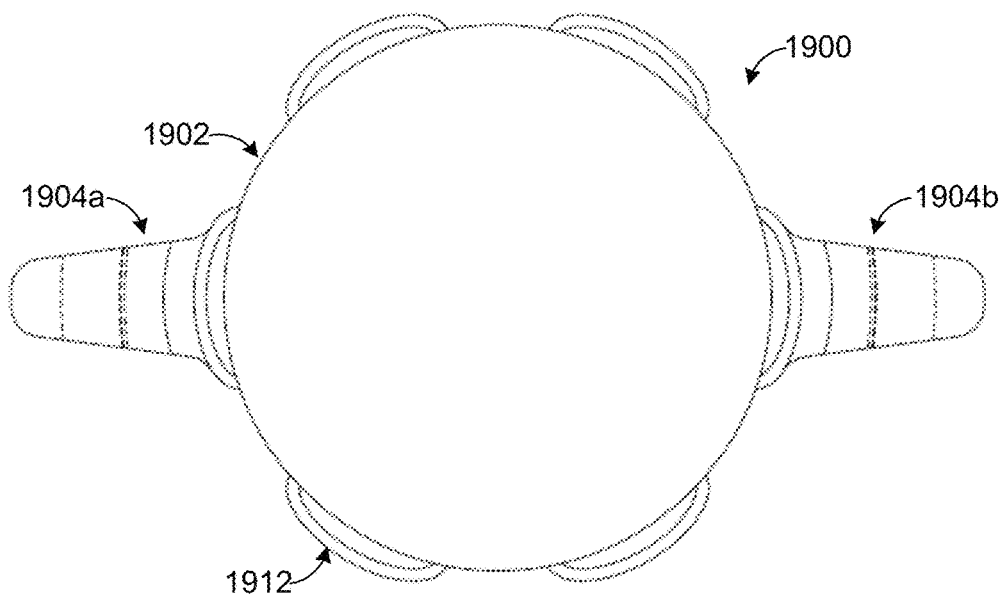
Figure 21:
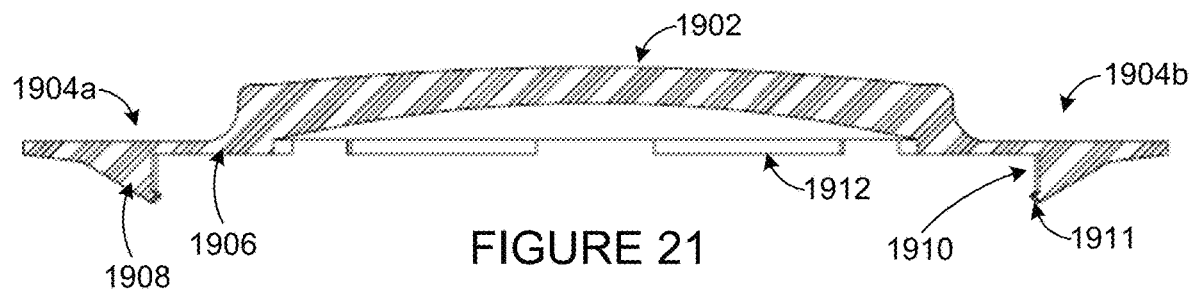

FIGS. 19 through 21 illustrate a ninth example intraocular pseudophakic contact lens 1900 according to this disclosure. In particular, FIG. 19 illustrates an oblique view of the intraocular pseudophakic contact lens 1900, FIG. 20 illustrates a top view of the intraocular pseudophakic contact lens 1900, and FIG. 21 illustrates a cross-sectional view through the middle of the intraocular pseudophakic contact lens 1900.

As shown in FIGS. 19 through 21, the intraocular pseudophakic contact lens 1900 has various components that are the same as or similar to those forming the intraocular pseudophakic contact lens 1600. For example, the intraocular pseudophakic contact lens 1900 includes an optical lens 1902 and multiple haptics 1904a-1904b. The haptics 1904a-1904b are formed by larger projections that extend from the sides of the optical lens 1902. Each haptic 1904a-1904b includes an inner portion 1906 that is connected to the optical lens 1902 (or to a retaining ring in which the optical lens 1902 is located) and an outer portion 1908 that is connected to the inner portion 1906. Each of the haptics 1904a-1904b also includes a ridge 1910, and multiple ridges 1910 of multiple haptics 1904a-1904b can be used to capture one or more edges of the underlying intraocular lens. In addition, the intraocular pseudophakic contact lens 1900 includes multiple segments 1912 along the sides of the optical lens 1902. The segments 1912 extend downward so that the bottom surfaces of the segments 1912 are located below the optical lens 1902.

The haptics 1904a-1904b in this example include thicker outer portions 1908 with larger ridges 1910 compared to the corresponding components of the intraocular pseudophakic contact lens 1600. This allows the haptics 1904a-1904b to be used with even larger intraocular lenses. Moreover, each of the ridges 1910 includes a lip 1911 that can facilitate the capture of the underlying intraocular lens. Each of the lips 1911 denotes any suitable inward projection from the corresponding ridge 1910.

Again, when implanted into a patient's eye, the segments 1912 help to keep the optical lens 1902 separated from the underlying intraocular lens. Depending on the shape of the posterior surface of the optical lens 1902 and the shape of the anterior surface of the underlying intraocular lens, this could elevate the optical lens 1902 over an optical lens within the underlying intraocular lens so that the optical lenses do not contact each other. The ability to space the optical lens 1902 away from the underlying intraocular lens could provide various benefits, such as those described above with respect to the intraocular pseudophakic contact lens 1600.

Figure 22:
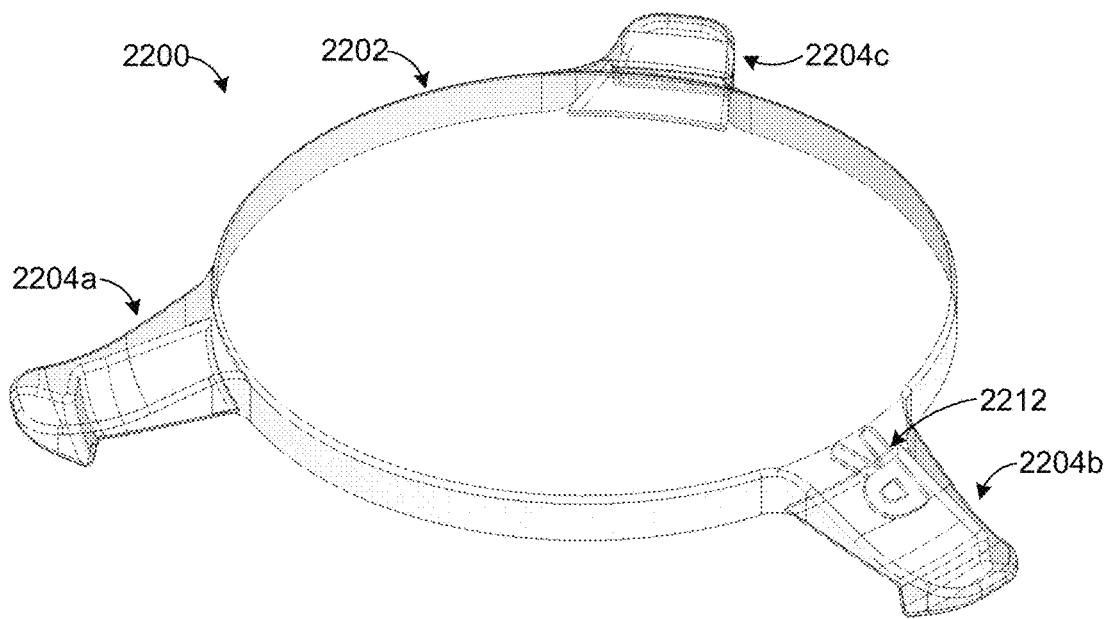
FIGS. 22 through 24 illustrate a tenth example intraocular pseudophakic contact lens according to this disclosure.
Figure 23:
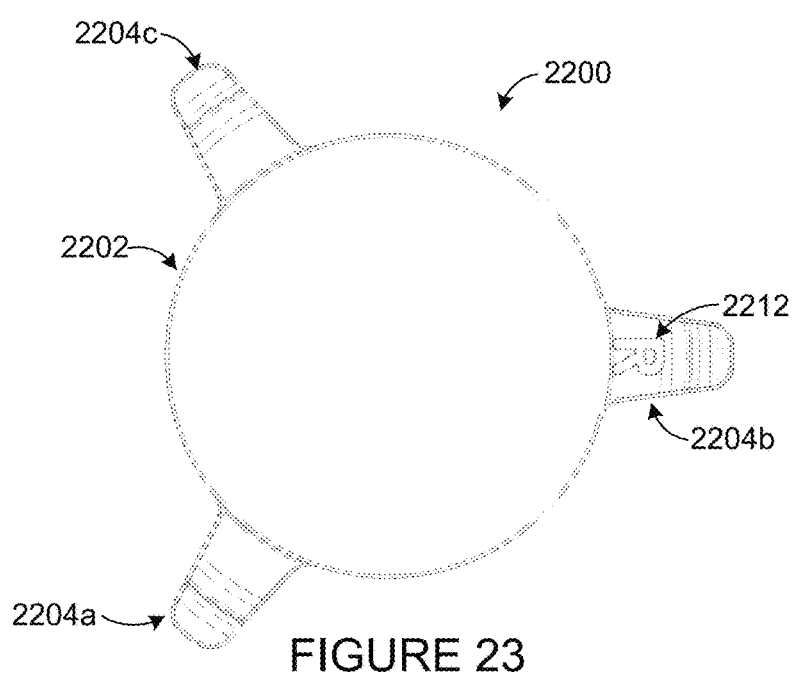
Figure 24:
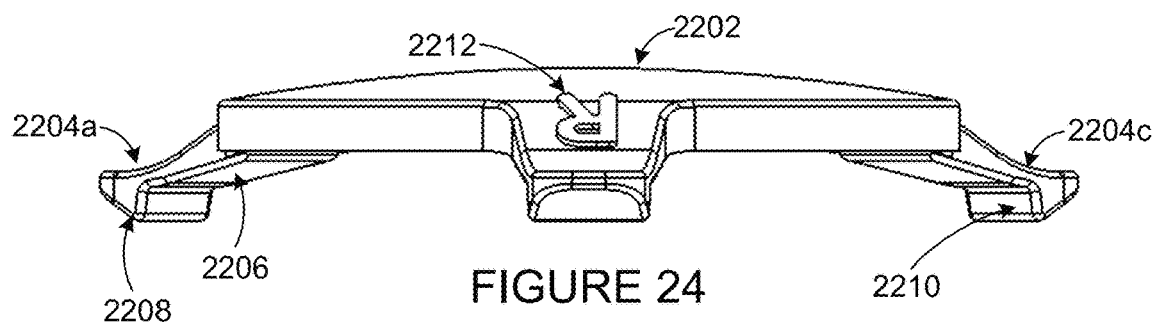

FIGS. 22 through 24 illustrate a tenth example intraocular pseudophakic contact lens 2200 according to this disclosure. In particular, FIG. 22 illustrates an oblique view of the intraocular pseudophakic contact lens 2200, FIG. 23 illustrates a top view of the intraocular pseudophakic contact lens 2200, and FIG. 24 illustrates a side view of the intraocular pseudophakic contact lens 2200.

As shown in FIGS. 22 through 24, the intraocular pseudophakic contact lens 2200 has various components that are the same as or similar to those forming the intraocular pseudophakic contact lens 1400. For example, the intraocular pseudophakic contact lens 2200 includes an optical lens 2202 and multiple haptics 2204a-2204c. The haptics 2204a-2204c are formed by projections that extend from the sides of the optical lens 2202. Each haptic 2204a-2204c includes an inner portion 2206 that is connected to the optical lens 2202 (or to a retaining ring in which the optical lens 2202 is located) and an outer portion 2208 that is connected to the inner portion 2206. Each of the haptics 2204a-2204c also includes a ridge 2210, and multiple ridges 2210 of multiple haptics 2204a-2204c can be used to capture one or more edges of the underlying intraocular lens. While not shown here, at least one of the ridges 2210 may include a lip, which can be the same as or similar to the lip 1911 and which can facilitate the capture and retention of the underlying intraocular lens.

In this example, the haptics 2204a-2204c are formed by large projections that extend from the sides of the optical lens 2202, where the projections have a thickness that tapers towards the outer edges of the projections. This facilitates easier insertion of the haptics 2204a-2204c under the anterior leaflet of the capsular wall in a patient's eye. Each of the haptics 2204a-2204c could include a textured surface, such as a number of holes or other structures, that promotes confinement, capture, or attachment to the anterior leaflet of the capsular wall. While three haptics 2204a-2204c are shown here, other numbers of haptics could also be used. In some embodiments, the haptics 2204a-2204c can be positioned at an even spacing of 120°.

Also in this example, an alignment marking 2212 is provided on one of the haptics 2204b. In this particular example, the alignment marking 2212 represents the letter "R," although any other suitable marking(s) may be used here in any suitable location(s). The alignment marking 2212 can be used to identify the proper orientation of the intraocular pseudophakic contact lens 2200, such as by identifying the haptic 2204b that is to be positioned on the right side of the intraocular pseudophakic contact lens 2200 (from the perspective of the surgeon or other medical personnel) after implantation.

Figure 25:
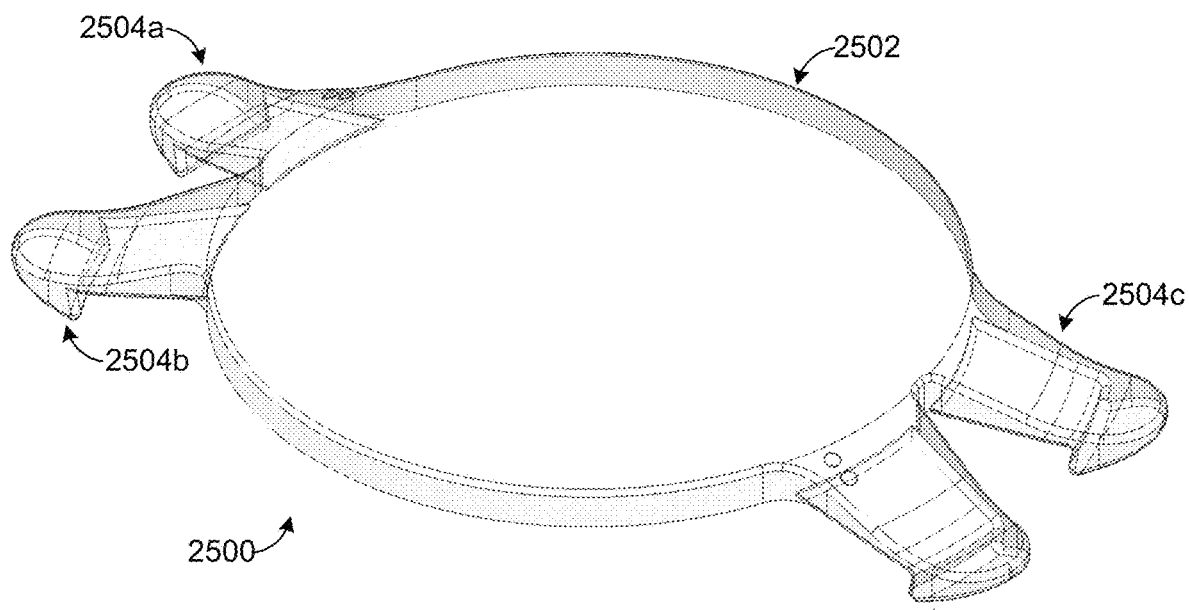
FIGS. 25 through 27 illustrate an eleventh example intraocular pseudophakic contact lens according to this disclosure.
Figure 26:
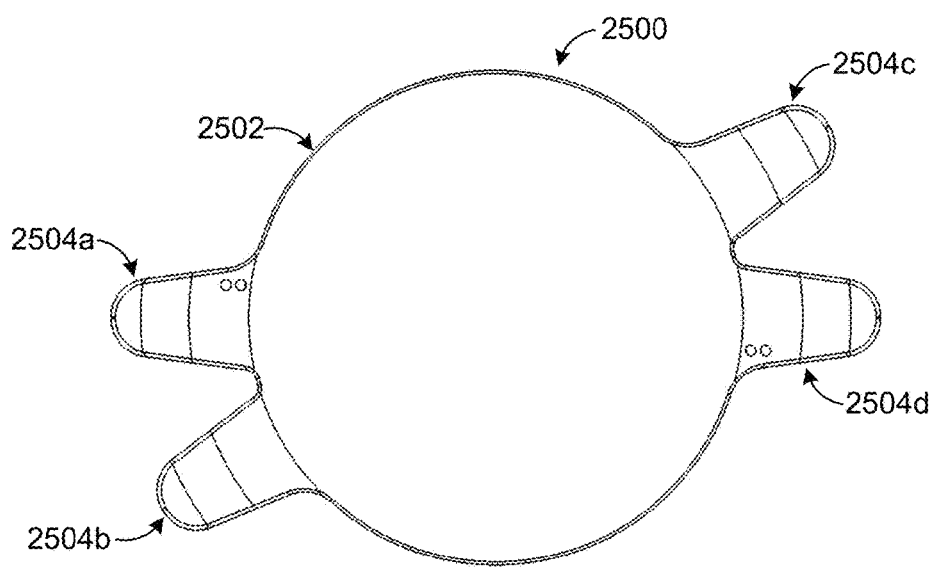
Figure 27:
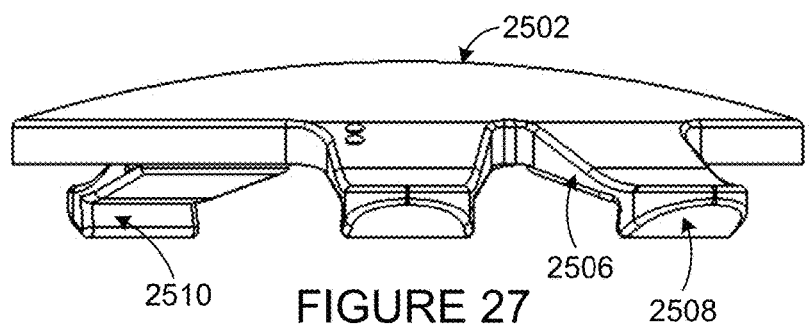

FIGS. 25 through 27 illustrate an eleventh example intraocular pseudophakic contact lens 2500 according to this disclosure. In particular, FIG. 25 illustrates an oblique view of the intraocular pseudophakic contact lens 2500, FIG. 26 illustrates a top view of the intraocular pseudophakic contact lens 2500, and FIG. 27 illustrates a side view of the intraocular pseudophakic contact lens 2500.

As shown in FIGS. 25 through 27, the intraocular pseudophakic contact lens 2500 has various components that are the same as or similar to those forming the intraocular pseudophakic contact lens 2200. For example, the intraocular pseudophakic contact lens 2500 includes an optical lens 2502 and multiple haptics 2504a-2504d. The haptics 2504a-2504d are formed by projections that extend from the sides of the optical lens 2502. Each haptic 2504a-2504d includes an inner portion 2506 that is connected to the optical lens 2502 (or to a retaining ring in which the optical lens 2502 is located) and an outer portion 2508 that is connected to the inner portion 2506. Each of the haptics 2504a-2504d also includes a ridge 2510, and multiple ridges 2510 of multiple haptics 2504a-2504d can be used to capture one or more edges of the underlying intraocular lens. While not shown here, at least one of the ridges 2510 may include a lip, which can be the same as or similar to the lip 1911 and which can facilitate the capture and retention of the underlying intraocular lens.

In this example, the haptics 2504a-2504d are formed by large projections that extend from the sides of the optical lens 2502, where the projections have a thickness that tapers towards the outer edges of the projections. This facilitates easier insertion of the haptics 2504a-2504d under the anterior leaflet of the capsular wall in a patient's eye. Each of the haptics 2504a-2504d could include a textured surface, such as a number of holes or other structures, that promotes confinement, capture, or attachment to the anterior leaflet of the capsular wall. While four haptics 2504a-2504d are shown here in two groups on opposite sides of the optical lens 2502, other numbers and arrangements of haptics could also be used.

Figure 28:
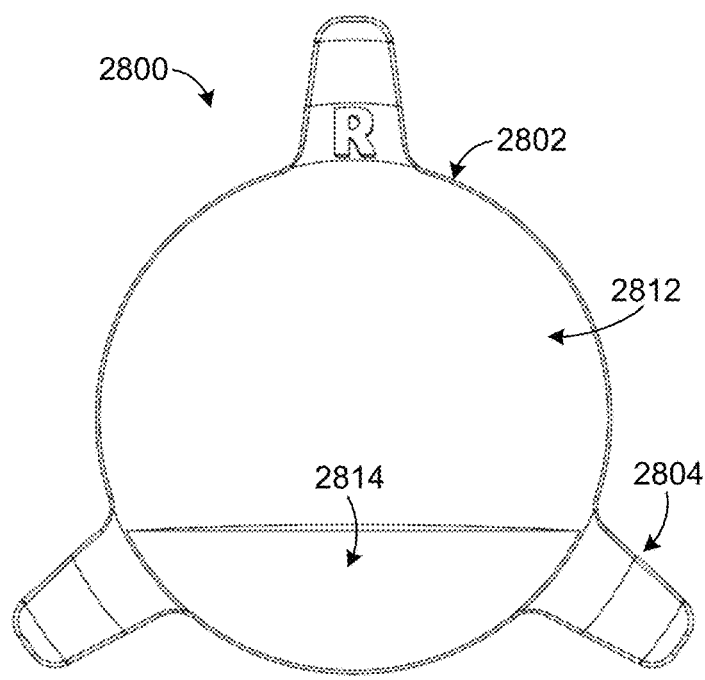
FIGS. 28 through 30 illustrate a twelfth example intraocular pseudophakic contact lens according to this disclosure.
Figure 29:
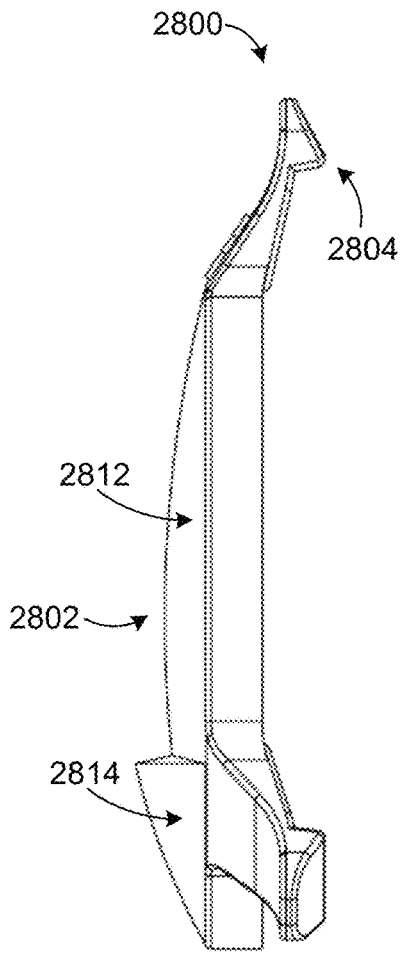
Figure 30:
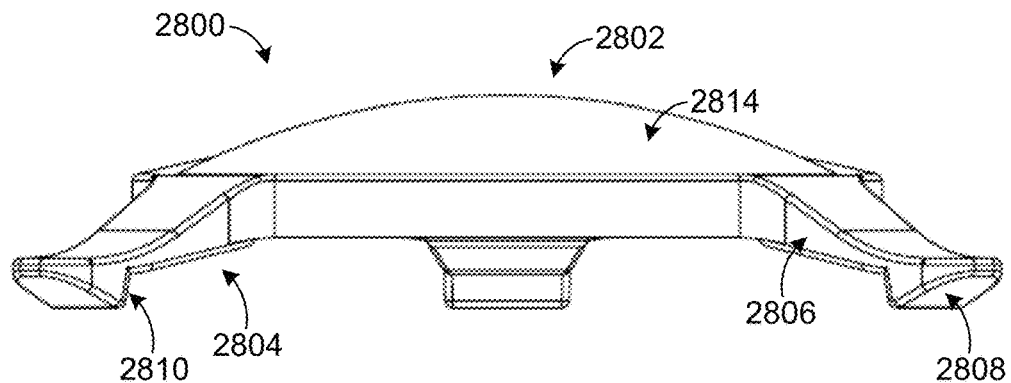

FIGS. 28 through 30 illustrate a twelfth example intraocular pseudophakic contact lens 2800 according to this disclosure. In particular, FIG. 28 illustrates a top view of the intraocular pseudophakic contact lens 2800, FIG. 29 illustrates a side view of the intraocular pseudophakic contact lens 2800, and FIG. 30 illustrates a bottom view of the intraocular pseudophakic contact lens 2800.

As shown in FIGS. 28 through 30, the intraocular pseudophakic contact lens 2800 has various components that are the same as or similar to those forming the intraocular pseudophakic contact lens 2200. For example, the intraocular pseudophakic contact lens 2800 includes an optical lens 2802 and multiple haptics 2804. The haptics 2804 are formed by projections that extend from the sides of the optical lens 2802. Each haptic 2804 includes an inner portion 2806 that is connected to the optical lens 2802 (or to a retaining ring in which the optical lens 2802 is located) and an outer portion 2808 that is connected to the inner portion 2806. Each of the haptics 2804 also includes a ridge 2810, and multiple ridges 2810 of multiple haptics 2804 can be used to capture one or more edges of the underlying intraocular lens. While not shown here, at least one of the ridges 2810 may include a lip, which can be the same as or similar to the lip 1911 and which can facilitate the capture and retention of the underlying intraocular lens.

In this example, the haptics 2804 are formed by large projections that extend from the sides of the optical lens 2802, where the projections have a thickness that tapers towards the outer edges of the projections. This facilitates easier insertion of the haptics 2804 under the anterior leaflet of the capsular wall in a patient's eye. Each of the haptics 2804 could include a textured surface, such as a number of holes or other structures, that promotes confinement, capture, or attachment to the anterior leaflet of the capsular wall. While three haptics 2804 are shown here, other numbers and arrangements of haptics could also be used.

In this example, the optical lens 2802 of the intraocular pseudophakic contact lens 2800 includes a first lens portion 2812 and a second lens portion 2814. The two portions 2812-2814 of the optical lens 2802 may be used to provide different levels of optical magnification. In this example, for instance, the first lens portion 2812 may provide a specified amount of magnification (or possibly little or no magnification), and the second lens portion 2814 may provide a higher specified amount of magnification. In some embodiments, the second lens portion 2814 may represent a "full seg" of added magnification compared to the first lens portion 2812. Note that the amount of magnification provided by each of the lens portions 2812-2814 may or may not be based on any residual refractive error in a patient's eye. Also note that while the lens portion 2814 with additional magnification is placed at the bottom of the optical lens 2802, a lens portion with additional magnification may be placed in any other suitable location(s) or along any other suitable axis or axes of the optical lens 2802. Further note that the sizes and shapes of the lens portions 2812-2814 can vary as needed or desired.

Figure 31:
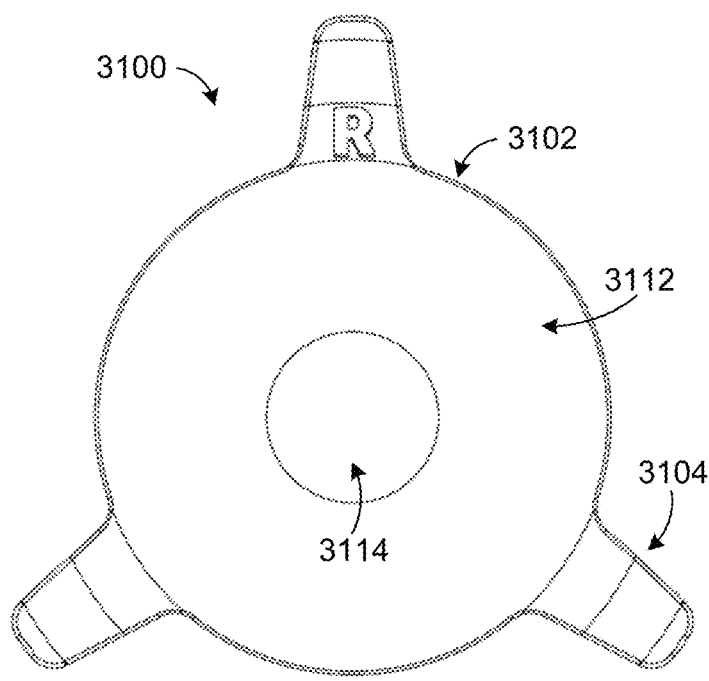
FIGS. 31 through 33 illustrate a thirteenth example intraocular pseudophakic contact lens according to this disclosure.
Figure 32:
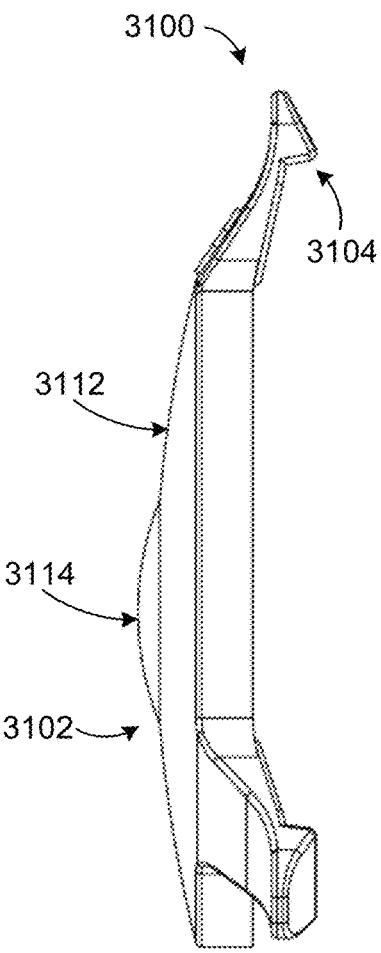
Figure 33:
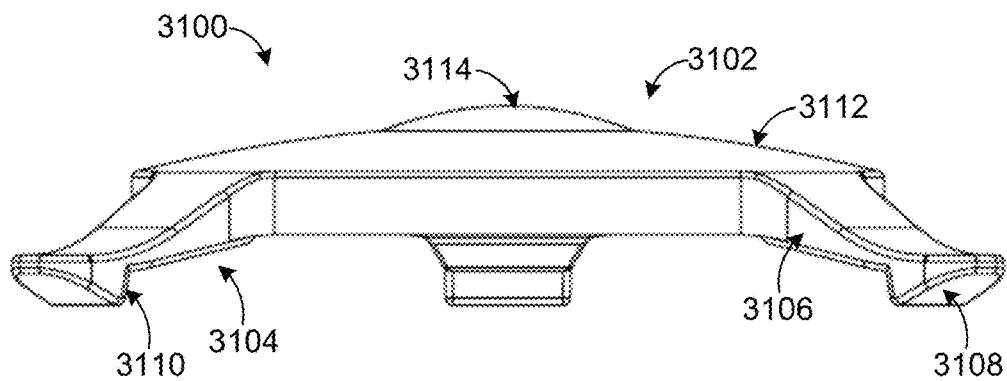

FIGS. 31 through 33 illustrate a thirteenth example intraocular pseudophakic contact lens 3100 according to this disclosure. In particular, FIG. 31 illustrates a top view of the intraocular pseudophakic contact lens 3100, FIG. 32 illustrates a side view of the intraocular pseudophakic contact lens 3100, and FIG. 33 illustrates a bottom view of the intraocular pseudophakic contact lens 3100.

As shown in FIGS. 31 through 33, the intraocular pseudophakic contact lens 3100 has various components that are the same as or similar to those forming the intraocular pseudophakic contact lens 2800. For example, the intraocular pseudophakic contact lens 3100 includes an optical lens 3102 and multiple haptics 3104. The haptics 3104 are formed by projections that extend from the sides of the optical lens 3102. Each haptic 3104 includes an inner portion 3106 that is connected to the optical lens 3102 (or to a retaining ring in which the optical lens 3102 is located) and an outer portion 3108 that is connected to the inner portion 3106. Each of the haptics 3104 also includes a ridge 3110, and multiple ridges 3110 of multiple haptics 3104 can be used to capture one or more edges of the underlying intraocular lens. While not shown here, at least one of the ridges 3110 may include a lip, which can be the same as or similar to the lip 1911 and which can facilitate the capture and retention of the underlying intraocular lens.

In this example, the haptics 3104 are formed by large projections that extend from the sides of the optical lens 3102, where the projections have a thickness that tapers towards the outer edges of the projections. This facilitates easier insertion of the haptics 3104 under the anterior leaflet of the capsular wall in a patient's eye. Each of the haptics 3104 could include a textured surface, such as a number of holes or other structures, that promotes confinement, capture, or attachment to the anterior leaflet of the capsular wall. While three haptics 3104 are shown here, other numbers and arrangements of haptics could also be used.

In this example, the optical lens 3102 of the intraocular pseudophakic contact lens 3100 includes a first lens portion 3112 and a second lens portion 3114. The two portions 3112-3114 of the optical lens 3102 may be used to provide different levels of optical magnification. In this example, for instance, the first lens portion 3112 may provide a specified amount of magnification (or possibly little or no magnification), and the second lens portion 3114 may provide a higher specified amount of magnification. Note that the amount of magnification provided by each of the lens portions 3112-3114 may or may not be based on any residual refractive error in a patient's eye. Also note that while the lens portion 3114 with additional magnification is placed in the center of the optical lens 3102, a lens portion with additional magnification may be placed in any other suitable location(s) or along any other suitable axis or axes of the optical lens 3102. Further note that the sizes and shapes of the lens portions 3112-3114 can vary as needed or desired.

Figure 34:
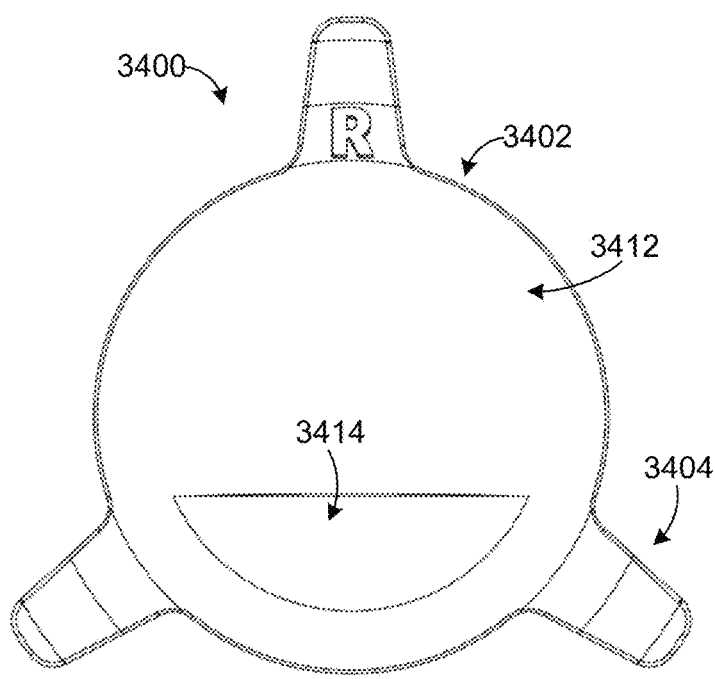
FIGS. 34 through 36 illustrate a fourteenth example intraocular pseudophakic contact lens according to this disclosure.
Figure 35:
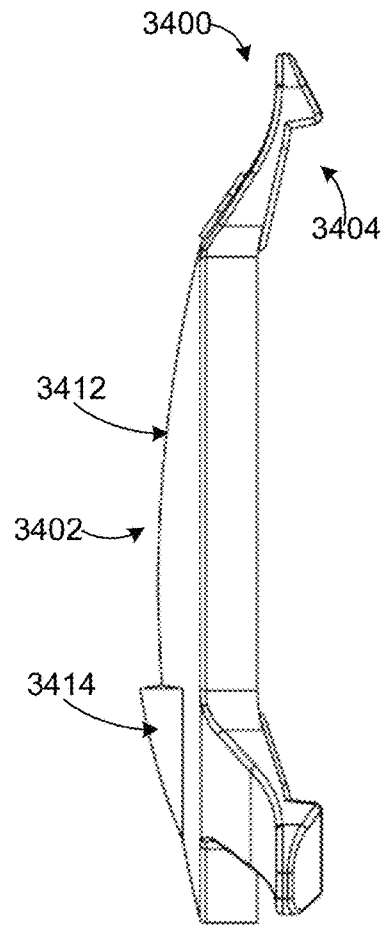
Figure 36:
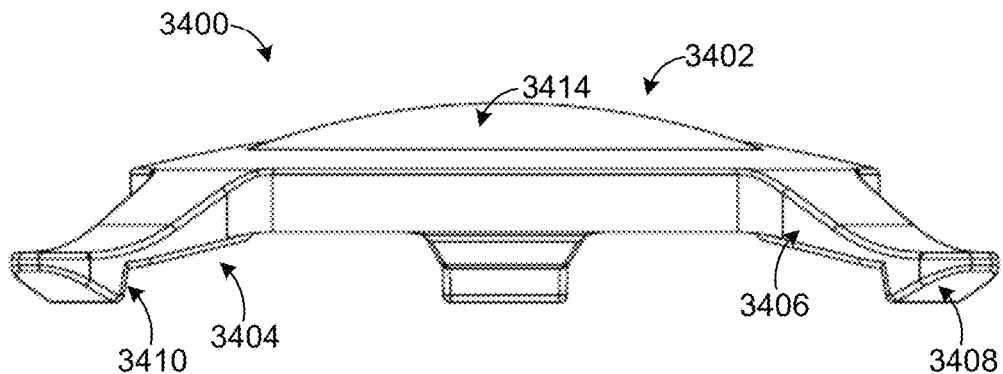

FIGS. 34 through 36 illustrate a fourteenth example intraocular pseudophakic contact lens 3400 according to this disclosure. In particular, FIG. 34 illustrates a top view of the intraocular pseudophakic contact lens 3400, FIG. 29 illustrates a side view of the intraocular pseudophakic contact lens 3400, and FIG. 36 illustrates a bottom view of the intraocular pseudophakic contact lens 3400.

As shown in FIGS. 34 through 36, the intraocular pseudophakic contact lens 3400 has various components that are the same as or similar to those forming the intraocular pseudophakic contact lens 2800. For example, the intraocular pseudophakic contact lens 3400 includes an optical lens 3402 and multiple haptics 3404. The haptics 3404 are formed by projections that extend from the sides of the optical lens 3402. Each haptic 3404 includes an inner portion 3406 that is connected to the optical lens 3402 (or to a retaining ring in which the optical lens 3402 is located) and an outer portion 3408 that is connected to the inner portion 3406. Each of the haptics 3404 also includes a ridge 3410, and multiple ridges 3410 of multiple haptics 3404 can be used to capture one or more edges of the underlying intraocular lens. While not shown here, at least one of the ridges 3410 may include a lip, which can be the same as or similar to the lip 1911 and which can facilitate the capture and retention of the underlying intraocular lens.

In this example, the haptics 3404 are formed by large projections that extend from the sides of the optical lens 3402, where the projections have a thickness that tapers towards the outer edges of the projections. This facilitates easier insertion of the haptics 3404 under the anterior leaflet of the capsular wall in a patient's eye. Each of the haptics 3404 could include a textured surface, such as a number of holes or other structures, that promotes confinement, capture, or attachment to the anterior leaflet of the capsular wall. While three haptics 3404 are shown here, other numbers and arrangements of haptics could also be used.

In this example, the optical lens 3402 of the intraocular pseudophakic contact lens 3400 includes a first lens portion 3412 and a second lens portion 3414. The two portions 3412-3414 of the optical lens 3402 may be used to provide different levels of optical magnification. In this example, for instance, the first lens portion 3412 may provide a specified amount of magnification (or possibly little or no magnification), and the second lens portion 3414 may provide a higher specified amount of magnification. In some embodiments, the second lens portion 3414 may represent a "small seg" of added magnification compared to the first lens portion 3412. Note that the amount of magnification provided by each of the lens portions 3412-3414 may or may not be based on any residual refractive error in a patient's eye. Also note that while the lens portion 3414 with additional magnification is placed near the bottom of the optical lens 3402, a lens portion with additional magnification may be placed in any other suitable location(s) or along any other suitable axis or axes of the optical lens 3402. Further note that the sizes and shapes of the lens portions 3412-3414 can vary as needed or desired.

While various prior approaches have secured an "add-on" lens to an intraocular lens, these prior approaches require a specific add-on lens to be designed for use with a specific intraocular lens and the specific intraocular lens to be designed for use with the specific add-on lens. That is, the add-on lens can only be used with a specific type of intraocular lens, where that intraocular lens is designed specifically for use with that add-on lens. As particular examples, an add-on lens may include haptics or other structures that are designed to mate with corresponding structures of specific intraocular lenses, or an intraocular lens may have a recess designed to receive a specific type of add-on lens. This can be problematic for a number of reasons. For instance, many patients already have existing intraocular lenses, and it may be impractical or even dangerous to try to remove those existing intraocular lenses in order to implant new intraocular lenses that are designed for use with add-on lenses.

The embodiments of the intraocular pseudophakic contact lenses shown in FIGS. 1 through 36 can help to alleviate these problems since the intraocular pseudophakic contact lenses can be secured over intraocular lenses by capturing and confining the haptics of the intraocular pseudophakic contact lenses using the anterior leaflets of capsular walls. In some cases, this could also involve physical bonding of the haptics to the anterior leaflets of capsular walls, such as via a fibrosis or re-fibrosis mechanism. In other words, the intraocular pseudophakic contact lenses do not need to be designed to work specifically with particular structures of any specific intraocular lens. The intraocular lens being used with an intraocular pseudophakic contact lens need not have any predefined structures that are provided for coupling to an intraocular pseudophakic contact lens. Rather, the intraocular pseudophakic contact lenses of FIGS. 1 through 36 can simply be sized so that, when the intraocular pseudophakic contact lens is placed on an intraocular lens, it can be secured in place through capture and confinement by (and possibly bonding with) the anterior leaflet of the capsular wall. This allows the intraocular pseudophakic contact lenses of FIGS. 1 through 36 to be used with a wide variety of intraocular lenses, including different types of intraocular lenses and including existing intraocular lenses already implanted into patients. There is no need to remove an existing intraocular lens from a patient in order to install a new intraocular lens and an intraocular pseudophakic contact lens.

Moreover, the intraocular pseudophakic contact lenses of FIGS. 1 through 36 could be easily removed from patients' eyes, such as any suitable time after implantation or prior to bonding of the haptics to the capsular walls (assuming fibrosis or re-fibrosis holds the intraocular pseudophakic contact lenses in place). Among other things, this allows one intraocular pseudophakic contact lens to be removed and replaced with a different intraocular pseudophakic contact lens if a different refractive correction or other vision correction is needed or desired.

The various intraocular pseudophakic contact lenses described above could have any suitable size, shape, and dimensions. For example, the intraocular pseudophakic contact lenses could be made available in a range of diameters from about 4 mm to about 6 mm. Also, the intraocular pseudophakic contact lenses could be made available with varying base curvatures for their optical lenses. Of course, an intraocular pseudophakic contact lens could also be custom designed for a particular patient's eye, such as when one or more specific curvatures are needed to correct for residual refractive error or to provide other desired vision correction in the particular patient's eye.

The intraocular pseudophakic contact lenses disclosed here can be implanted non-invasively in patients' eyes and easily positioned on intraocular lenses. The implantation is non-invasive because an intraocular pseudophakic contact lens is being installed on the anterior surface of an intraocular lens, which is typically easily accessible by a surgeon or other personnel during an implantation procedure. The implantation is also non-invasive because the intraocular pseudophakic contact lenses can be attached to intraocular lenses without requiring attachment of the intraocular pseudophakic contact lenses to anatomical structures within the patients' eyes, such as to the suculus of a patient's eye.

The non-invasive implantation and easy positioning of an intraocular pseudophakic contact lens provide a safe and effective refractive surgical procedure to correct unwanted residual refractive error or provide some other desired vision correction, such as after a lensectomy procedure. As a refractive modality, the intraocular pseudophakic contact lenses contribute to a surgeon's ability to alter the current refractive error of a pseudophakic patient or otherwise alter the vision of the pseudophakic patient in an effort to adjust the patient's vision to achieve a finely-tuned desired refraction. Specific examples of this functionality include allowing adjustments to a patient's eye in order to achieve unilateral or bilateral emmetropia, to induce unilateral myopia to allow for intermediate and near visual function, to introduce multi-focality, and to treat unwanted residual astigmatism.

If the haptics of an intraocular pseudophakic contact lens include ridges along their bottom surfaces, the ridges can be used to center the intraocular pseudophakic contact lens on an underlying intraocular lens as described above. If the intraocular pseudophakic contact lens includes three haptics with associated ridges, the ridges could help to perfectly center the intraocular pseudophakic contact lens on the underlying intraocular lens. Such an approach allows the ridges of the intraocular pseudophakic contact lens' haptics to capture the underlying intraocular lens at the edge and perfectly line up the optical center of the intraocular pseudophakic contact lens' optic with the optical center of the intraocular lens. This alignment helps to reduce or avoid induced optical aberrations or induced prisms caused by optical center misalignment. This provides a strong contributing benefit over conventional refractive fine-tuning modalities.

Note that in any of the above examples, the intraocular pseudophakic contact lens could possibly be designed so that only the haptics of the intraocular pseudophakic contact lens extend under the anterior leaflet of the capsular wall in a patient's eye. This allows the haptics to be captured and confined by the anterior leaflet while leaving the optical lens of the intraocular pseudophakic contact lens free and generally unobscured by the surrounding tissue in the patient's eye.

Also note that, in some embodiments, the surgical tool disclosed in U.S. patent application Ser. No. 16/280,235 (which is hereby incorporated by reference in its entirety) may be used to help implant an intraocular pseudophakic contact lens. For example, this tool may be used to separate at least part of the anterior leaflet of a patient's eye from an implanted intraocular lens, allowing haptics of the intraocular pseudophakic contact lens to be inserted between the anterior leaflet and the intraocular lens. As another example, this tool may be used to separate the anterior leaflet of a patient's eye from an implanted intraocular pseudophakic contact lens, allowing the intraocular pseudophakic contact lens to be removed (and possibly replaced).

In addition, it should be appreciated from the description above that a wide variety of optical lenses or other optical devices may be used as the optical lens of any given intraocular pseudophakic contact lens. This enables intraocular pseudophakic contact lenses to be used to provide a wide variety of vision corrections in patients' eyes when joined with intraocular lenses in the patients' eyes. As noted above, for example, intraocular pseudophakic contact lenses may be used to help correct myopia, hyperopia, and/or astigmatism refractive errors in patients' eyes. As other examples, intraocular pseudophakic contact lenses may be used to provide magnification for low-vision patients, to provide guided focal points by way of adjusted prisms, and/or to provide variable apertures (such as pin holes, cat's eye structures, and/or stenopaeic slits). As other examples, intraocular pseudophakic contact lenses may be used to provide various forms of vision correction (such as multi-focal, astigmatic, depth of focus, asymmetrical cornea, and/or photochromic correction), to provide for drug delivery, to provide UV protection, and/or to support dysphotopsia treatment. In general, this disclosure is not limited to any specific types or shapes of optical lenses in intraocular pseudophakic contact lens or to any specific types of treatments using intraocular pseudophakic contact lens.

Although FIGS. 1 through 36 illustrate examples of intraocular pseudophakic contact lens, various changes may be made to FIGS. 1 through 36. For example, any suitable combination of features shown in FIGS. 1 through 36 could be used together in a single intraocular pseudophakic contact lens, whether or not that specific combination of features is shown in the figures or described above. As a particular example, any of the intraocular pseudophakic contact lenses shown in FIGS. 1 through 36 could include one or more pins at one or more desired locations, one or more ridges along the bottom surface(s) of its haptic(s) to aid in the capture of an intraocular lens and centration on the intraocular lens, and/or one or more lips to help capture the intraocular lens. Also, each intraocular pseudophakic contact lens could include any suitable number of each component shown in any of the figures. While the figures have shown the intraocular pseudophakic contact lenses as having two, three, or four haptics (some at an even spacing of 120° or 180°), any number of haptics (with or without associated pins, ridges, lips, or other structures) could be used. Further, the forms of the haptics shown here are examples only, and any other suitable structures could be used to capture, confine, or attach to the anterior leaflet of a capsular wall in a patient's eye. In addition, a number of other features could be used at one or more locations of the intraocular pseudophakic contact lenses. For instance, one or more alignment markings could be provided to identify proper alignment of the intraocular pseudophakic contact lens with the intraocular lens, or one or more drug-eluting materials could be placed on top, side, or bottom surfaces of the optical lenses in the intraocular pseudophakic contact lenses.

Figure 37:
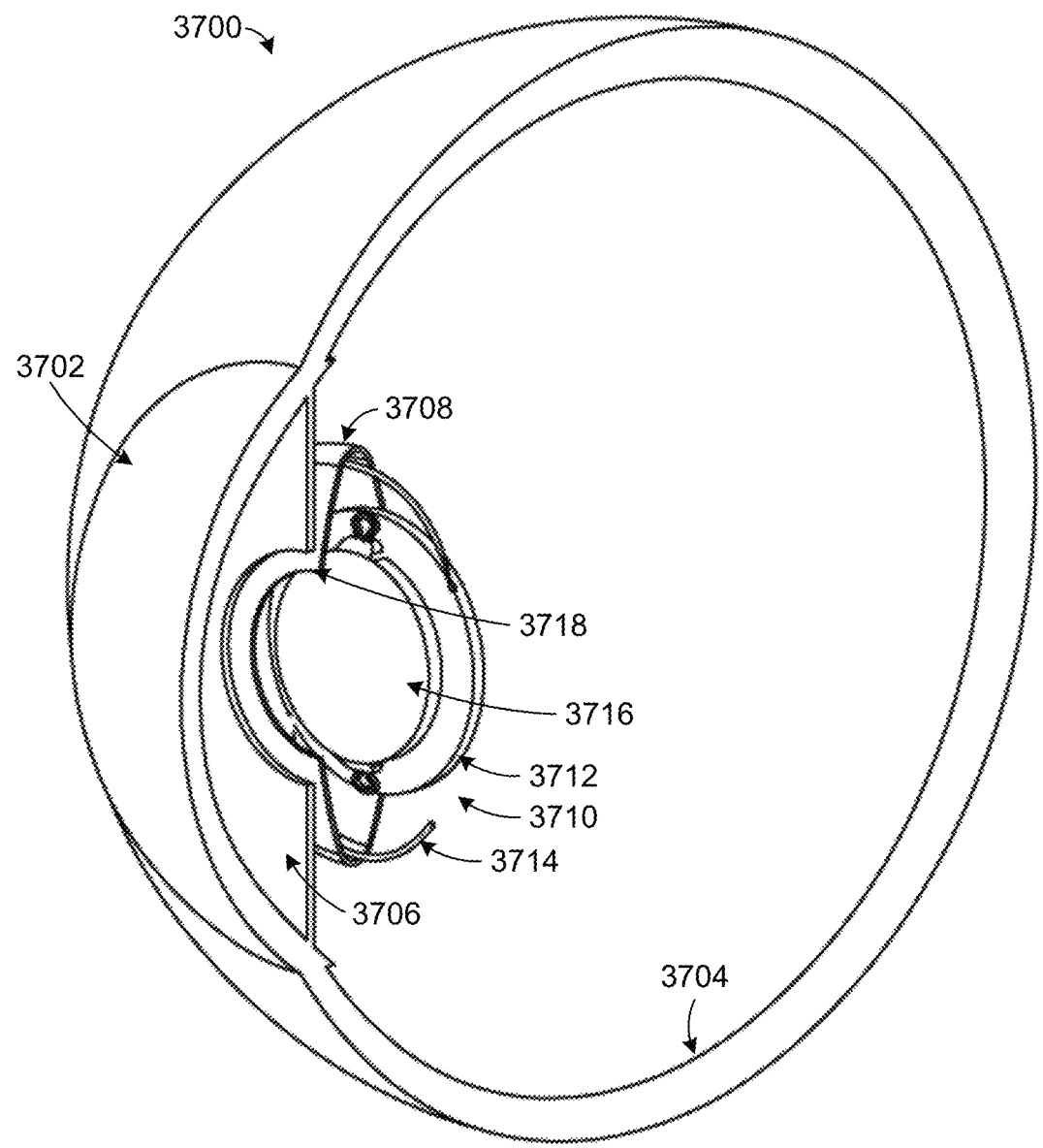
FIG. 37 illustrates an example intraocular lens and an example intraocular pseudophakic contact lens in a patient's eye according to this disclosure.

FIG. 37 illustrates an example intraocular lens and an example intraocular pseudophakic contact lens in a patient's eye 3700 according to this disclosure. As shown in FIG. 37, the eye 3700 includes a cornea 3702, a sclera 3704, and an iris 3706. The cornea 3702 represents the clear front portion of the eye 3700 through which light passes to enter into the eye 3700. The sclera 3704 is the tough outer white portion of the eye. The iris 3706 controls the size of the eye's pupil to thereby control the amount of light from the cornea 3702 that enters into the interior of the eye 3700.

The eye 3700 also includes a capsular bag 3708, which typically holds the natural crystalline lens of the eye 3700. However, in this example, the natural crystalline lens has been removed and replaced with an intraocular lens 3710 having an optical lens 3712 and one or more haptics 3714. The optical lens 3712 of the intraocular lens 3710 receives light entering the eye and focuses the light onto the retina of the eye 3700. The haptics 3714 of the intraocular lens 3710 help to hold the intraocular lens 3710 within the capsular bag 3708 so that the optical lens 3712 of the intraocular lens 3710 is in a desired position within the eye.

An intraocular pseudophakic contact lens 3716 has also been placed on the intraocular lens 3710 within the capsular bag 3708. The intraocular pseudophakic contact lens 3716 can represent any of the intraocular pseudophakic contact lenses described above or any other suitable intraocular pseudophakic contact lens. The intraocular pseudophakic contact lens 3716 is placed on the anterior surface of the intraocular lens 3710, meaning the front surface of the intraocular lens 3710 with respect to the eye 3700. Light enters through the cornea 3702 and passes through the pupil before entering the intraocular pseudophakic contact lens 3716, which modifies the light. The modified light then passes through the optical lens 3712 of the intraocular lens 3710 and is again modified. The twice-modified light then travels through the remainder of the eye 3700 to reach the retina at the back of the eye 3700.

As described above, the intraocular pseudophakic contact lens 3716 includes one or more haptics that extend a short distance and fit under an anterior leaflet 3718 of the capsular bag 3708. This allows the haptics to be captured and confined by the anterior leaflet 3718 (and possibly attach to the anterior leaflet 3718 via fibrosis or re-fibrosis). The anterior leaflet 3718 represents the outer portion of the front side of the capsular bag 3708 that remains after a capsulorhexis is formed in the capsular bag 3708. The insertion of the haptics of the intraocular pseudophakic contact lens 3716 under the anterior leaflet 3718 helps to secure the intraocular pseudophakic contact lens 3716 in place. In some cases, the healing process in the eye 3700 can cause fibrosis to occur, which could also attach the anterior leaflet 3718 to the haptics of the intraocular pseudophakic contact lens 3716.

Note that the haptics of the intraocular pseudophakic contact lens 3716 are shorter or smaller than the haptics 3714 of the intraocular lens 3710. This is because the haptics 3714 of the intraocular lens 3710 extend generally to the top and bottom of the capsular bag 3708 and help to hold the intraocular lens 3710 in the proper position within the capsular bag 3708. The haptics of the intraocular pseudophakic contact lens 3716 need not extend to the top and bottom of the capsular bag 3708 and instead may only extend a short distance under the anterior leaflet 3718.

By properly selecting the optical lens of the intraocular pseudophakic contact lens 3716, the intraocular pseudophakic contact lens 3716 can ideally correct any residual refractive error that remains after implantation of the intraocular lens 3710 or provide any other desired vision correction in the patient's eye 3700. If necessary, the intraocular pseudophakic contact lens 3716 can also be removed and replaced with a different intraocular pseudophakic contact lens. This may be needed or desired if the intraocular pseudophakic contact lens 3716 does not properly correct the residual refractive error, if the intraocular pseudophakic contact lens 3716 actually causes additional refractive errors, or if some other form of vision correction is needed or desired.

Although FIG. 37 illustrates one example of an intraocular lens and one example of an intraocular pseudophakic contact lens in a patient's eye, various changes may be made to FIG. 37. For example, the intraocular lens 3710 could be attached to any other intraocular pseudophakic contact lens. Also, there are a number of intraocular lenses available, and an intraocular pseudophakic contact lens could be coupled to any other suitable intraocular lens in the eye 3700.

Figure 38:
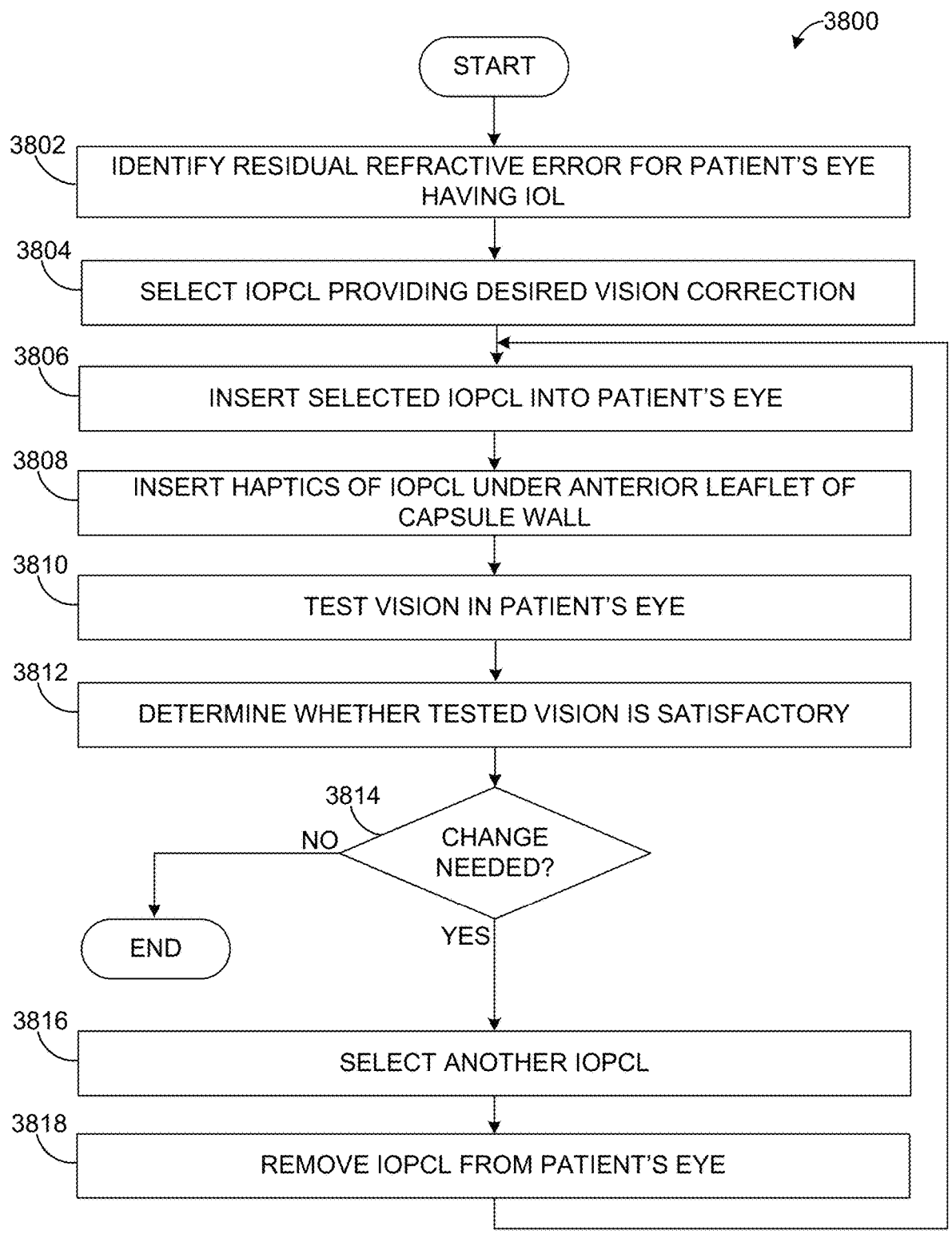
FIG. 38 illustrates an example method for using an intraocular pseudophakic contact lens with an intraocular lens according to this disclosure.

FIG. 38 illustrates an example method 3800 for using an intraocular pseudophakic contact lens with an intraocular lens according to this disclosure. As shown in FIG. 38, residual refractive error in a patient's eye having an intraocular lens is identified at step 3802. This could include, for example, personnel testing the patient's vision and identifying any refractive error that remains after implantation of the intraocular lens 3710. The testing could be done in any suitable manner, such as by using intraoperative wavefront aberrometry. One goal of the testing can be to identify what refractive errors exist in the patient's eye after implantation of the intraocular lens in the patient's eye. This testing could be performed at any suitable time, such as after a lensectomy procedure. Note, however, that this step is optional since an intraocular pseudophakic contact lens may be used to provide other forms of vision correction in a patient's eye and does not necessarily need to correct a residual refractive error.

An intraocular pseudophakic contact lens (IOPCL) is selected, such as to correct the identified residual refractive error or to provide some other form of vision correction, at step 3804. This could include, for example, personnel selecting an intraocular pseudophakic contact lens from a kit, where the selected intraocular pseudophakic contact lens has an optical lens that substantially neutralizes the identified residual refractive error. This could also include the personnel selecting an optical lens from a kit and inserting the optical lens into an intraocular pseudophakic contact lens, where the selected optical lens substantially cancels the identified residual refractive error. This could further include the personnel obtaining an intraocular pseudophakic contact lens having a custom-designed optical lens or obtaining a custom-designed optical lens for insertion into an intraocular pseudophakic contact lens, where the custom-designed optical lens substantially cancels the identified residual refractive error. In addition, this could include the personnel obtaining (in whatever manner) an intraocular pseudophakic contact lens that provides a desired amount of magnification, multi-focality, or other form of vision correction. In general, any mechanism can be used to obtain a suitable intraocular pseudophakic contact lens.

The selected intraocular pseudophakic contact lens is inserted into the patient's eye at step 3806. This could include, for example, a surgeon or other personnel forming a small incision in the patient's eye and inserting the intraocular pseudophakic contact lens into the eye through the incision. The intraocular pseudophakic contact lens can be rolled, folded, or otherwise reduced in cross-sectional size in order to insert the intraocular pseudophakic contact lens through a smaller incision.

One or more haptics of the intraocular pseudophakic contact lens are inserted under the anterior leaflet of the capsular wall in the patient's eye at step 3808. This could include, for example, the surgeon or other personnel placing the intraocular pseudophakic contact lens 3716 at a desired position (and possibly in a desired orientation) on the intraocular lens 3710. This could also include the surgeon or other personnel moving the intraocular pseudophakic contact lens 3716 so that its haptics (in whatever form) slide under the anterior leaflet 3718 of the capsular bag 3708.

A vision test for the patient occurs at step 3810. The vision test could be done in any suitable manner, such as by using intraoperative wavefront aberrometry. This vision test could also be performed at any suitable time, such as during the surgical procedure in which the intraocular pseudophakic contact lens is being implanted or after the surgical procedure has been completed. A determination is made whether the tested vision is satisfactory at step 3812. This could include, for example, personnel determining whether the patient's eye is still experiencing any residual refractive error and, if so, to what extent. This could also include personnel determining whether the patient's eye requires additional magnification, multi-focality, or other form of vision correction.

A determination is made whether to change the intraocular pseudophakic contact lens at step 3814. This could include, for example, the personnel and the patient determining whether the remaining residual refractive error (if any) is inconvenient or otherwise problematic for the patient or otherwise determining whether the current vision correction is inadequate. If so, different steps could be taken to try and fix the problem. For instance, the currently-implanted intraocular pseudophakic contact lens could be repositioned to adjust for cylinder axis correction. If that fails, another intraocular pseudophakic contact lens is selected at step 3816. This could include, for example, personnel selecting another intraocular pseudophakic contact lens that (ideally) provides a better refractive correction or other vision correction for the patient's eye compared to the currently-inserted intraocular pseudophakic contact lens. The currently-inserted intraocular pseudophakic contact lens is removed from the patient's eye at step 3818. This could include, for example, the surgeon or other personnel sliding the haptics of the currently-inserted intraocular pseudophakic contact lens 3716 from under the anterior leaflet 3718 and removing the currently-inserted intraocular pseudophakic contact lens 3716 from the patient's eye. The process then returns to step 3806, where the newly-selected intraocular pseudophakic contact lens can be inserted into the patient's eye and the vision test can be repeated.

After the process shown in FIG. 38 is over, the haptics of the implanted intraocular pseudophakic contact lens 3716 can be captured/confined by the anterior leaflet 3718 of the capsular bag 3708 in the patient's eye. This helps to hold the intraocular pseudophakic contact lens 3716 in place. Moreover, the healing process in the patient's eye can optionally cause fibrosis or re-fibrosis to occur, which could physically attach the haptics of the implanted intraocular pseudophakic contact lens 3716 to the anterior leaflet 3718 of the capsular bag 3708.

Although FIG. 38 illustrates one example of a method 3800 for using an intraocular pseudophakic contact lens with an intraocular lens, various changes may be made to FIG. 38. For example, while shown as a series of steps, various steps in FIG. 38 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in this patent document should not be read as implying that any particular element, step, or function is an essential or critical element that must be included in the claim scope. Also, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   an intraocular pseudophakic contact lens comprising:
   an optical lens; and
   haptics extending radially from the optical lens and configured to be inserted under an anterior leaflet of a capsular wall in an eye in order to capture and confine the haptics under the anterior leaflet and secure the intraocular pseudophakic contact lens against an artificial intraocular lens in the eye;
   wherein anterior surfaces of the haptics comprise capsular wall-engaging surfaces configured to contact an inner capsular wall surface at the anterior leaflet, the capsular wall-engaging surfaces configured to promote confinement, capture, or attachment of the haptics;
   wherein posterior surfaces of the haptics comprise ridges configured to capture at least one edge of the artificial intraocular lens in order to secure the intraocular pseudophakic contact lens to the artificial intraocular lens; and
   wherein different portions of the optical lens provide different amounts of magnification such that a first portion of the optical lens provides a first amount of magnification and a second portion of the optical lens provides a second amount of magnification.

2. The apparatus of claim 1, wherein:
the first portion of the optical lens provides a specified amount of magnification; and
the second portion of the optical lens provides less or no magnification.

3. The apparatus of claim 1, wherein:
the first portion of the optical lens provides a specified amount of magnification and forms a central region of the optical lens; and
the second portion of the optical lens provides less or no magnification relative to the specified amount of magnification and forms an annular region around the first portion of the optical lens.

4. The apparatus of claim 1, wherein:
the first portion of the optical lens provides a specified amount of magnification and forms a lower portion of the optical lens, the first portion of the optical lens having an upper boundary extending straight across the optical lens; and
the second portion of the optical lens provides less or no magnification relative to the specified amount of magnification and forms a remaining portion of the optical lens above the first portion of the optical lens.

5. The apparatus of claim 1, wherein:
the first portion of the optical lens provides a specified amount of magnification and is positioned in a lower portion of the optical lens, the first portion of the optical lens having an upper boundary extending straight across part of the optical lens; and
the second portion of the optical lens provides less or no magnification relative to the specified amount of magnification and is positioned above and around the first portion of the optical lens.

6. The apparatus of claim 1, wherein the ridge of each haptic comprises a lip projecting from the ridge and extending inward from the ridge.

7. The apparatus of claim 1, wherein the optical lens is configured to at least partially correct a residual refractive error in the eye, the residual refractive error comprising a refractive error that exists in the eye after implantation of the artificial intraocular lens in the eye.

8. The apparatus of claim 1, wherein the first and second amounts of magnification are not based on a residual refractive error in the eye.

9. The apparatus of claim 1, wherein the intraocular pseudophakic contact lens comprises at least three haptics extending radially from the optical lens.

10. A system comprising:
an artificial intraocular lens comprising a first optical lens and first haptics configured to be implanted within a capsular bag in an eye; and
an intraocular pseudophakic contact lens comprising:
a second optical lens; and
second haptics extending radially from the second optical lens and configured to be inserted under an anterior leaflet of a capsular wall in the eye in order to capture and confine the second haptics under the anterior leaflet and secure the intraocular pseudophakic contact lens against the artificial intraocular lens in the eye;
wherein anterior surfaces of the second haptics comprise capsular wall-engaging surfaces configured to contact an inner capsular wall surface at the anterior leaflet, the capsular wall-engaging surfaces configured to promote confinement, capture, or attachment of the haptics;
wherein posterior surfaces of the second haptics comprise ridges configured to capture at least one edge of the artificial intraocular lens in order to secure the intraocular pseudophakic contact lens to the artificial intraocular lens; and
wherein different portions of the second optical lens provide different amounts of magnification such that a first portion of the second optical lens provides a first amount of magnification and a second portion of the second optical lens provides a second amount of magnification.

11. The system of claim 10, wherein:
the first portion of the second optical lens provides a specified amount of magnification; and
the second portion of the second optical lens provides less or no magnification.

12. The system of claim 10, wherein:
the first portion of the second optical lens provides a specified amount of magnification and forms a central region of the second optical lens; and
the second portion of the second optical lens provides less or no magnification relative to the specified amount of magnification and forms an annular region around the first portion of the second optical lens.

13. The system of claim 10, wherein:
the first portion of the second optical lens provides a specified amount of magnification and forms a lower portion of the second optical lens, the first portion of the second optical lens having an upper boundary extending straight across the second optical lens; and
the second portion of the second optical lens provides less or no magnification relative to the specified amount of magnification and forms a remaining portion of the second optical lens above the first portion of the second optical lens.

14. The system of claim 10, wherein:
the first portion of the second optical lens provides a specified amount of magnification and is positioned in a lower portion of the second optical lens, the first portion of the second optical lens having an upper boundary extending straight across part of the second optical lens; and
the second portion of the second optical lens provides less or no magnification relative to the specified amount of magnification and is positioned above and around the first portion of the second optical lens.

15. The system of claim 10, wherein the ridge of each haptic comprises a lip projecting from the ridge and extending inward from the ridge.

16. The system of claim 10, wherein the second optical lens is configured to at least partially correct a residual refractive error in the eye, the residual refractive error comprising a refractive error that exists in the eye after implantation of the artificial intraocular lens in the eye.

17. The system of claim 10, wherein the first and second amounts of magnification are not based on a residual refractive error in the eye.

18. The system of claim 10, wherein the intraocular pseudophakic contact lens comprises at least three second haptics extending radially from the second optical lens.

19. The system of claim 10, wherein the second haptics are shorter than the first haptics.

20. An apparatus comprising:
an intraocular pseudophakic contact lens comprising:
an optical lens; and
at least three haptics extending radially from the optical lens and configured to be inserted under an anterior leaflet of a capsular wall in an eye in order to capture and confine the haptics under the anterior leaflet and secure the intraocular pseudophakic contact lens against an artificial intraocular lens in the eye;

wherein anterior surfaces of the haptics comprise capsular wall-engaging surfaces configured to contact an inner capsular wall surface at the anterior leaflet, the capsular wall-engaging surfaces configured to promote confinement, capture, or attachment of the haptics;

wherein posterior surfaces of the haptics comprise ridges and lips projecting inward from the ridges, the ridges and lips configured to capture at least one edge of the artificial intraocular lens in order to secure the intraocular pseudophakic contact lens to the artificial intraocular lens;

wherein each of the haptics comprises an inner portion and an outer portion;

wherein the inner portion of each haptic is positioned between the optical lens and the outer portion of the haptic;

wherein the inner portion of each haptic projects outward and posteriorly from the optical lens;

wherein, for each haptic, the ridge is defined where a larger thickness of the outer portion of the haptic meets a smaller thickness of the inner portion of the haptic; and wherein different portions of the optical lens provide different amounts of magnification such that a first portion of the optical lens provides a specified amount of magnification and a second portion of the optical lens provides less or no magnification relative to the specified amount of magnification.

\* \* \* \* \*